(12) United States Patent
Creaven et al.

(10) Patent No.: US 9,925,045 B2
(45) Date of Patent: Mar. 27, 2018

(54) SYSTEMS, DEVICES AND METHODS FOR TRANSCATHETER VALVE DELIVERY

(71) Applicant: Medtronic Vascular Galway, Ballybrit, Galway (IE)

(72) Inventors: Marian Creaven, Ballybrit (IE); Marc Anderson, Ballybrit (IE); Kate Corish, Ballybrit (IE); Declan Costello, Ballybrit (IE); Niall Duffy, Ballybrit (IE); Joshua Dwork, Santa Rosa (CA); John Gallagher, Ballybrit (IE); Patrick Griffin, Ballybrit (IE); Gavin Kenny, Ballybrit (IE); Deirdre McGowan Smyth, Ballybrit (IE); John Milroy, Ballybrit (IE); Jason Quill, Forest Lake, MN (US); Herinaina Rabarimanantsoa Jamous, Ballybrit (IE); Paul Rothstein, Elk River, MN (US); Jeffrey Sandstrom, Scandia, MN (US); Edmond Sheahan, Ballybrit (IE); Frank White, Ballybrit (IE)

(73) Assignee: Medtronic Vascular Galway, Galway (IE)

( * ) Notice: Subject to any disclaimer, the term of this patent is extended or adjusted under 35 U.S.C. 154(b) by 453 days.

(21) Appl. No.: 14/519,242

(22) Filed: Oct. 21, 2014

(65) Prior Publication Data
US 2015/0112430 A1    Apr. 23, 2015

Related U.S. Application Data

(60) Provisional application No. 61/893,399, filed on Oct. 21, 2013.

(51) Int. Cl.
A61F 2/24        (2006.01)

(52) U.S. Cl.
CPC .......... *A61F 2/2436* (2013.01); *A61F 2/2439* (2013.01); *A61F 2/2418* (2013.01)

(58) Field of Classification Search
CPC .... A61F 2/2436; A61F 2/2439; A61F 2/2427; A61F 2/2466
See application file for complete search history.

(56) References Cited

U.S. PATENT DOCUMENTS

| | | |
|---|---|---|
| 5,957,949 A | 9/1999 | Leonhardt et al. |
| 7,147,657 B2 | 12/2006 | Chiang et al. |
| 7,988,724 B2 | 8/2011 | Salahieh et al. |
| 8,157,852 B2 | 4/2012 | Bloom et al. |
| 8,167,932 B2 | 5/2012 | Bourang et al. |
| 8,337,541 B2 | 12/2012 | Quadri et al. |
| 2010/0049313 A1 | 2/2010 | Alon et al. |

(Continued)

*Primary Examiner* — Thomas McEvoy

(57) ABSTRACT

A heart valve therapy system including a delivery device and a stented valve. The delivery device includes an outer sheath, an inner shaft, an optional hub assembly, and a plurality of tethers. In a delivery state, a stent frame of the prosthesis is crimped over the inner shaft and maintained in a compressed condition by the outer sheath. The tethers are connected to the stent frame. In a partial deployment state, the outer sheath is at least partially withdrawn, allowing the stent frame to self-expand. Tension in the tethers prevents the stent frame from rapidly expanding and optionally allowing recapture. Upon completion of the stent frame expansion, the tethers are withdrawn.

17 Claims, 22 Drawing Sheets

(56) References Cited

U.S. PATENT DOCUMENTS

2010/0121434 A1* 5/2010 Paul ................. A61F 2/2418
                                                        623/2.11
2011/0060404 A1   3/2011 Malewicz et al.
2011/0106246 A1   5/2011 Malewicz et al.
2011/0264198 A1* 10/2011 Murray, III ......... A61F 2/2418
                                                        623/2.11
2011/0301702 A1  12/2011 Rust et al.

* cited by examiner

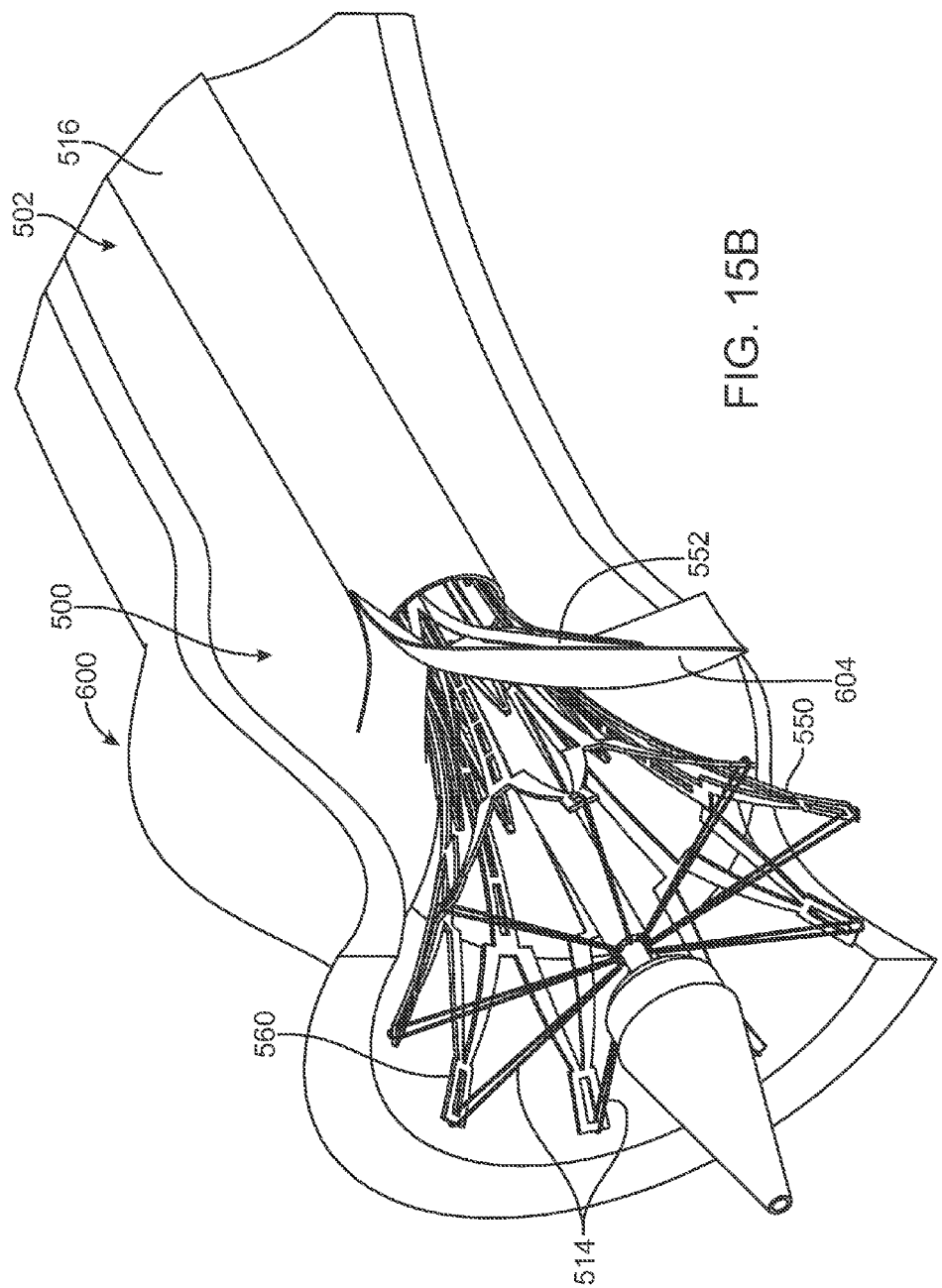

SYSTEMS, DEVICES AND METHODS FOR TRANSCATHETER VALVE DELIVERY

CROSS REFERENCE TO RELATED APPLICATIONS

This Non-Provisional Patent Application claims the benefit of the filing dates of U.S. Provisional Patent Application Ser. No. 61/893,399, filed Oct. 21, 2013, entitled "SYSTEMS, DEVICES AND METHODS FOR TRANSCATHETER VALVE DELIVERY," the entire teachings of which are incorporated herein by reference.

BACKGROUND

The present disclosure relates to delivery devices for implanting transcatheter valves. More particularly, it relates to catheter-based delivery devices and methods for implanting a prosthetic heart valve with controlled release of the prosthesis from the delivery device.

Diseased or otherwise deficient heart valves can be repaired or replaced using a variety of different types of heat valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a lumen within the patient, such as the femoral artery, and delivered to a desired location in the heart.

The heart valve prosthesis employed with catheter-based, or transcatheter, procedures generally includes an expandable multi-level frame or stent that supports a valve body having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site.

The actual shape or configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the native anatomy. With self-expanding stent designs, the stent frame can experience significant, rapid radial expansion upon deployment from the sheath. Taken in combination, these design features can give rise to delivery concerns. A rapidly expanding stent having one section expanding to a substantially larger diameter than an adjacent section can cause the prosthetic heart valve to spring off a valve retainer of the delivery device in a relatively un-controlled fashion. This rapid deployment can, in turn, result in the valve section(s) forcing itself past or beyond the intended anatomical location. For example, exemplary prosthetic mitral valve designs can have an inflow diameter on the order of 60 mm, with the inflow section of the stent frame being perpendicular, or nearly perpendicular, to a shape of the outflow section. During transluminal delivery to the native mitral valve, the stent frame is crimped down to a nearly cylindrical shape, having a diameter on the order of 12 mm. The inflow section of the prosthetic mitral valve is intended to self-engage the native annulus, can experience rapid, uncontrolled expansion upon deployment, and may instead thrust past the native annulus and into the left ventricle.

Although there have been multiple advances in transcatheter prosthetic heart valves and related delivery systems and techniques, there is a continuing need to provide different delivery tools for controlled deployment of the prosthesis.

SUMMARY

Some aspects of the present disclosure relate to systems for performing a therapeutic procedure on a defective heart valve, and include a delivery device and a stented prosthetic heart valve. The delivery device includes an outer sheath assembly, an inner shaft assembly, and a plurality of tethers. The prosthetic heart valve includes a stent frame that is configured to self-expand from a compressed condition to a normal, expanded condition. In a delivery state of the system, the stent frame is crimped over the inner shaft assembly (for example on to a valve retainer and/or a valve support), and is constrained in a compressed condition by the outer sheath assembly. Further, the tethers are connected to the stent frame, with at least one end of the tether being routed proximally toward a handle assembly of the delivery device. Arrangement of the stent frame relative to the delivery device defines a proximal portion and a distal portion, with the tethers being connected to the proximal portion or the distal portion. In some embodiments, the tethers are looped about struts or other structures provided by the stent frame. In related embodiments, a free end of each tether is connected to a valve retainer body along the inner shaft assembly; in other embodiments, the both ends of each tether are routed to the handle assembly. In yet other embodiments, a leading end of each tether is directly connected to the stent frame. Regardless, during use in delivering the stented prosthetic heart valve to a native valve, the system is transitioned to a partial deployment state in which the sheath assembly is at least partially retracted from over the stent frame, removing the constraining force imparted upon the stent frame. The exposed portion(s) of the stent frame self-expand toward the normal, expanded condition, with a tension in the tethers preventing the corresponding region of the stent frame from rapidly expanding. Upon attaining complete expansion, the delivery device is transitioned to a full deployment state in which the tethers are withdrawn from the stent frame. In some embodiments, the systems and devices of the present disclosure provide for recapture of an expanded stent frame prior to release of the tethers, for example by re-tensioning the tethers to effectuate at least partial compression or re-collapsing of the corresponding region of the stent frame. The stent frame can then more easily be received within a separate recapture sheath or the delivery sheath.

DETAILED DESCRIPTION

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame having an internal one maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when release from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1A:
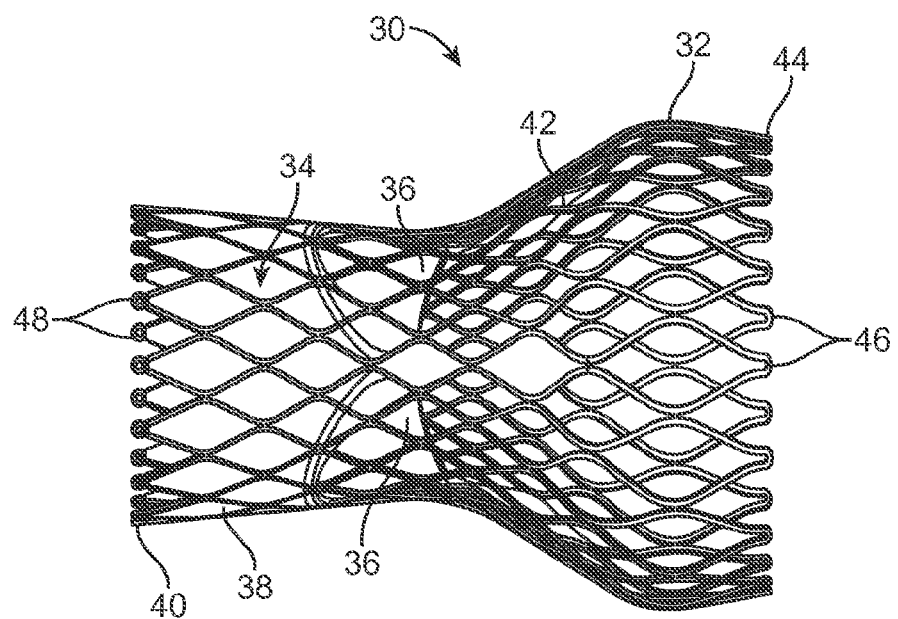
FIG. 1A is a side view of an exemplary stented prosthetic heart valve useful with systems, devices and methods of the present disclosure and in a normal, expanded condition.
Figure 1B:
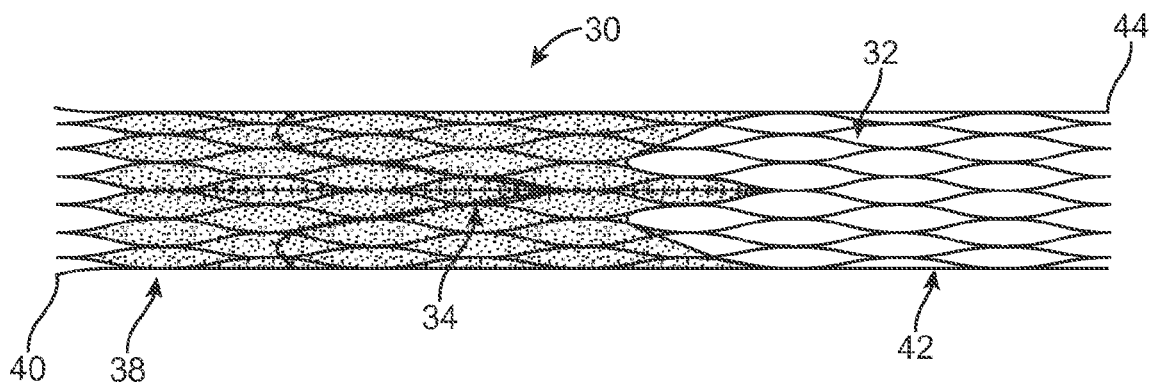
FIG. 1B is a side view of the prosthetic heart valve of FIG. 1A in a compressed condition.

With the above understanding in mind, one simplified, non-limiting example of a stented prosthetic heart valve 30 useful with systems, devices and methods of the present disclosure is illustrated in FIG. 1A. As a point of reference, the prosthetic heart valve 30 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 30 includes a stent or stent frame 32 and a valve structure 34. The stent frame 32 can assume any of the forms mentioned above, and is generally constructed so as to be self-expandable from the compressed condition (FIG. 1B) to the normal, expanded condition (FIG. 1A).

The valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 can be formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve. In some constructions, the valve structure 34 can comprise two or three leaflets that are fastened together at enlarged lateral end regions to form commissural joints, with the unattached edges forming coaptation edges of the valve structure 34. The leaflets 36 can be fastened to a skirt that in turn is attached to the frame 32. The upper ends of the commissure points can define an inflow portion 38 corresponding to a first or inflow end 40 of the prosthesis 30. The opposite end of the valve can define an outflow portion 42 corresponding to a second or outflow end 44 of the prosthesis 30. As shown, the stent frame 32 can have a lattice or cell-like structure, and forms or provides crowns 46 and/or eyelets 48 (or other shapes) at the outflow and inflow ends 40, 44.

Figure 2:
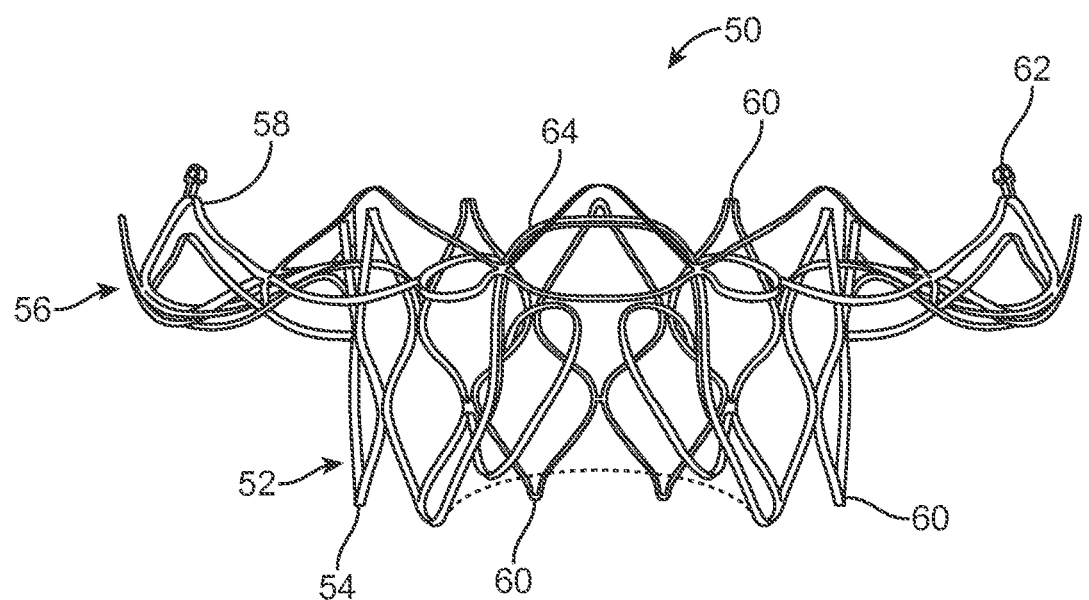
FIG. 2 is a side view of another exemplary prosthetic heart valve stent useful with systems, devices and methods of the present disclosure and in a normal, expanded condition.

With the but one acceptable construction of FIGS. 1A and 1B, the prosthetic heart valve 30 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 2 illustrates another non-limiting example of a stent frame 50 portion of another prosthetic heart valve with which the systems, devices and methods of the present disclosure are useful. In the normal or expanded condition of FIG. 2, the stent frame 50 can be sized and shaped for mitral valve implantation. Though not shown, the valve structure attached to the stent frame 50 defines an outflow portion 52 arranged at a first or outflow end 54, and an inflow portion 56 arranged at a second or inflow end 58. As compared to the stent frame 32 of FIG. 1A, the inflow portion 56 can exhibit a more pronounced change in shape relative to the corresponding outflow portion 52. Regardless, the stent frame 50 can be forced and constrained to a compressed condition (not shown, but akin to the shape of FIG. 1A) during delivery, and will self-expand to the natural condition of FIG. 2 upon removal of the constraining force(s). As a point of reference, in some constructions, the stent frame 50 is configured to be crimped to a diameter on the order of 12 mm during delivery, and will self-expand to the natural, expanded condition that includes the inflow portion 56 having a diameter on the order of 60 mm. As reflected in FIG. 2, crowns 60 and/or eyelets 62 (or other shapes) can be formed at one or both of the outflow and inflow ends 54, 58. Further, the stent frame 50 can optionally include or carry additional structural components, such as support arm(s) 64.

Figure 3A:
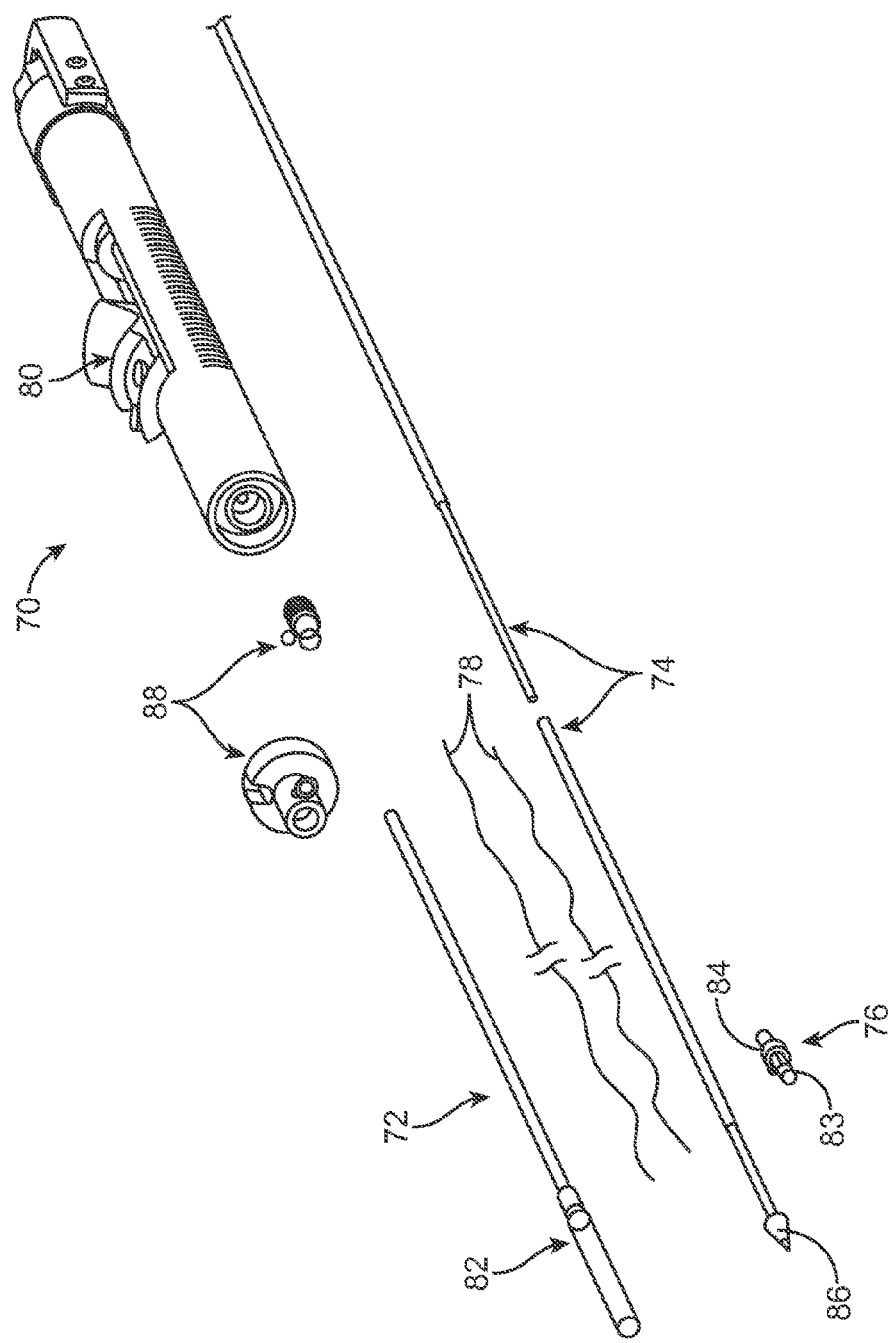
FIG. 3A is an exploded perspective view of a stented prosthetic heart valve delivery device in accordance with principles of the present disclosure.
Figure 3B:
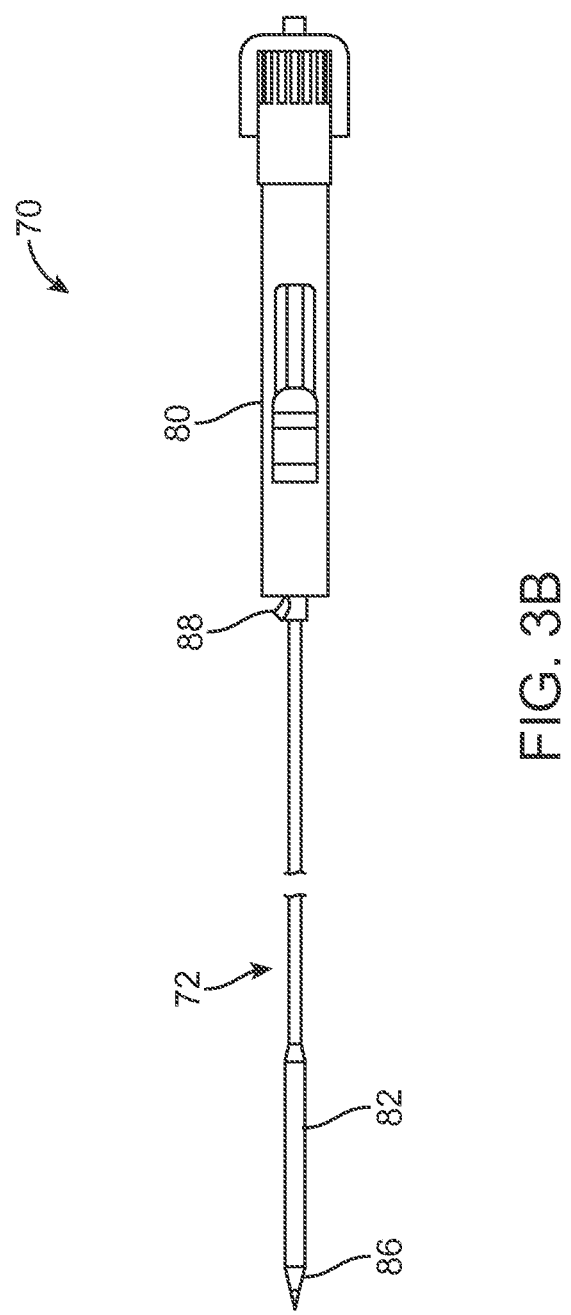
FIG. 3B is a side view of the delivery device of FIG. 3A.

With the above understanding of the stented prosthetic heart valves in mind, one embodiment of a delivery device 70 for percutaneously delivering the prosthesis is shown in simplified form in FIGS. 3A and 3B. The delivery device 70 includes a delivery sheath assembly 72, an inner shaft assembly 74, a hub assembly 76, one or more tethers 78, and a handle assembly 80. Details on the various components are provided below. In general terms, however, the delivery device 70 combines with a stented prosthetic heart valve (not shown) to form a system for performing a therapeutic procedure on a defective heart valve of a patient. The delivery device 70 provides a loaded or delivery state in which a stented prosthetic heart valve is coupled to the inner shaft assembly 74 via the hub assembly 76 and compressively retained within a capsule 82 of the delivery sheath assembly 72. For example, the hub assembly 76 can include or provide one or both of a valve support 83 and a valve retainer 84. The valve retainer 84 is configured to selectively receive a corresponding feature (e.g., posts) provided with the prosthetic heart valve stent frame, whereas the valve support 83 provides an increased diameter (as compared to a diameter of the inner shaft assembly 74) for directly supporting a portion of a length of the stent frame in the compressed condition. The valve support 83 and the valve retainer 84 can be formed as separate components, or can be integrally formed. In yet other embodiments, the hub assembly 76 does not include the valve support 83, or does not include the valve retainer 84. As used throughout this disclosure, then, a "hub assembly component" is in reference to a valve support, a valve retainer, or both, and the corresponding delivery device need only include one of the valve support or the valve retainer. The tether(s) 78 connect an end of the stented prosthetic heart valve to a remainder of the delivery device 70, for example to the hub assembly 76. The delivery sheath assembly 72 can be manipulated to withdraw the capsule 82 proximally from over the prosthetic heart valve via operation of the handle assembly 80, permitting the prosthesis to self-expand and partially release from the inner shaft assembly 74 in a partial deployment state. In the partial deployment state, the tether(s) 78 maintain connection between the prosthesis and the delivery device 70 (e.g., connection with the hub assembly 76) such that expansion of the corresponding portion or end of the stented prosthetic heart valve is controlled and/or is less than complete in some embodiments. In other embodiments, the tether(s) 78 slowly self-releases from the stent frame as the stent frame expands in a manner that reduces the rate at which expansion occurs (e.g., the tethers 78 effectuate slow release of the stent frame from the delivery device 70). With configurations in which the tether(s) 78 remains connected to the stent frame upon retraction of the capsule 82, the tether(s) 78 can optionally be subjected to increased tension, causing the corresponding portion of the stent frame to at least partially re-collapse or compress, making recapture of the stent frame possible (e.g., recapture within a separate recapture sheath (not shown) advanced over the delivery sheath assembly 72, or back within the capsule 82). In a deployment state, the tether(s) 78 is removed from engagement with the prosthesis, permitting the stented prosthetic heart valve to completely release or deploy from the delivery device 70.

Various features of the components 72-80 reflected in FIGS. 3A and 3B and as described below can be modified or replaced with differing structures and/or mechanisms. Thus, the present disclosure is in no way limited to the delivery sheath assembly 72, the inner shaft assembly 74, the hub assembly 76 or the handle assembly 80 as shown. Any construction that generally facilitates compressed loading of a stented prosthetic heart valve over an inner shaft via a retractable outer sheath or capsule is acceptable. For example, the capsule 82 may be a discrete component of the delivery sheath assembly 72, or can be more homogeneously formed as part of a continuous outer sheath. The inner shaft assembly 74 can integrally form the hub assembly 76 (including one or both of the valve support 83 and the valve retainer 84) and can terminate in a dilator tip 86. Further, the tether(s) 78 can also assume a wide variety of forms and arrangements relative to a remainder of the delivery device 70 as described below. The tether(s) 78 can be a suture, thread, thin wire, or other elongated, flexible body. Finally, the delivery device 70 can include additional components or features, such as a flush port assembly 88, a recapture sheath (not shown), etc.

Figure 4A:
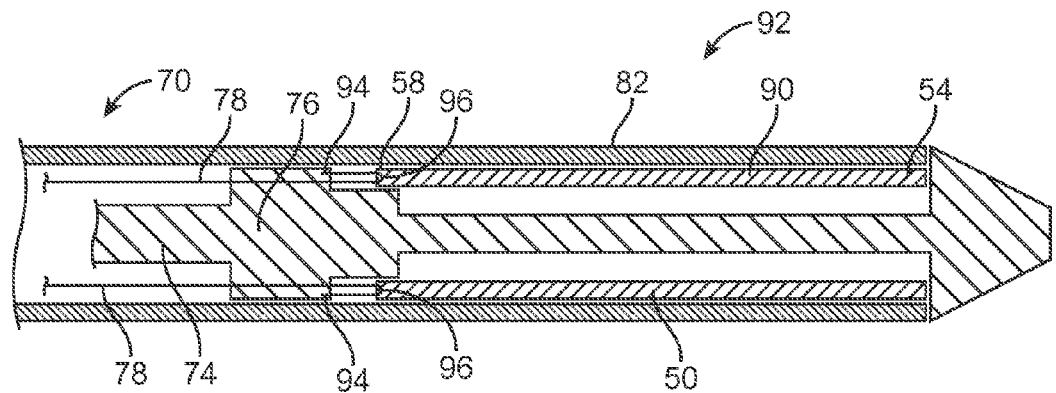
FIG. 4A is a simplified, cross-sectional view of a portion of a delivery device in accordance with principles of the present disclosure, loaded with a stented prosthetic heart valve and in a delivery state.

In more general terms, a simplified representation of one embodiment of the delivery device 70 in the delivery state and loaded with a stented prosthetic heart valve 90 (referenced generally) to provide a system 92 for performing a therapeutic procedure on a defective heart valve is provided in FIG. 4A. For ease of illustration, only the stent frame 50 of the prosthesis 90 is depicted in FIG. 4A. The stent frame 50 is crimped over the inner shaft assembly 74, and is compressibly held in the compressed condition by the capsule 82. The prosthesis 90 is arranged such that the inflow end 58 is proximal the outflow end 54. As loaded to the delivery device 70, then, the inflow end 58 can be viewed as the proximal end of the prosthesis 90, and the outflow end 54 as the distal end. In other embodiments, an orientation of the prosthetic heart valve 90 can be reversed relative to the delivery device 70. One or more of the tethers 78 are connected to the proximal end 58. For example, in the view of FIG. 4A, two of the tethers 78 are provided, it being understood that in other embodiments, only a single tether 78 or more than two of the tethers 78 is included. Each of the tethers 78 defines a leading end 94 opposite a trailing end (not shown). A leading segment 96 is defined immediately adjacent the leading end 94. With these designations in mind, the leading segment 96 is looped through a portion of the stent frame 50 at or adjacent the proximal end 58, for example through one of the crowns 60 or eyelets 62 (FIG. 2). The leading end 94 is connected to the hub assembly 76 (e.g., at a valve retainer such as the valve retainer 84 (FIG. 3A)), with the capsule 82 (or other portion of the delivery sheath assembly 72) serving to capture the leading end 94 to the hub assembly 76. The trailing end of each of the tethers 78 can be positioned in various locations, and in some embodiments is routed proximally to the handle assembly 80 (FIGS. 3A and 3B). In this regard, the hub assembly 76 can form a corresponding number of passageways through which the tethers 78 extend, respectively.

Figure 4B:
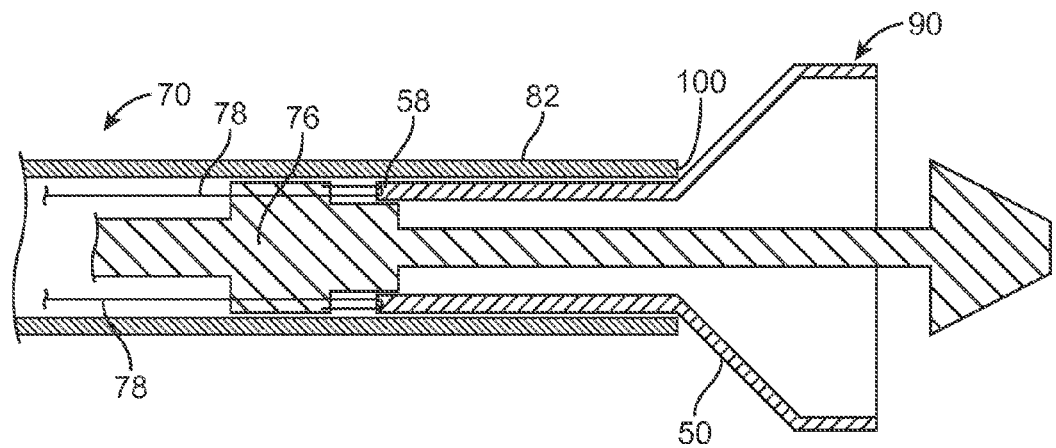
FIGS. 4B-4E illustrate operation of the delivery device of FIG. 4A in transiting to a partial deployment state and a full deployment state.

Following transluminal delivery of the compressed prosthesis 90 to the targeted native valve (via the delivery device 70 in the delivery state of FIG. 4A), the delivery device 70 is operated to deploy the stented prosthetic heart valve 90 by proximally retracting the capsule 82. FIG. 4B illustrates an initial stage of deployment in which the capsule 82 has been partially retracted from over the prosthesis 90. As shown, a portion of the prosthesis 90 is still within the capsule 82 (e.g., a distal end 100 of the capsule 82 is distal the proximal end 58 of the stented prosthetic heart valve 90). The now-exposed segment of the prosthesis 90 distal the capsule 82 self-expands to or toward the normal or expanded condition. That portion of the prosthesis 90 still within the confines of the capsule 82 remains in the compressed condition and is thus still captured or robustly connected to the delivery device 70. Further, the capsule 82 maintains the captured arrangement of the tethers 78 with the hub assembly 76, and thus with the stent frame 50.

Figure 4C:
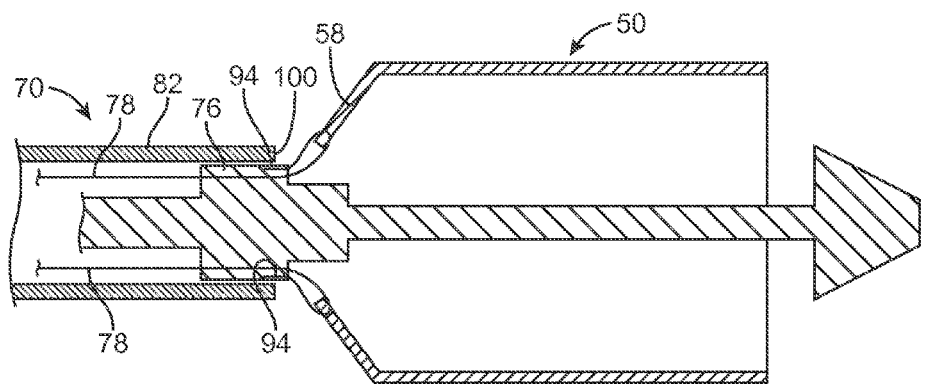
Figure 4D:
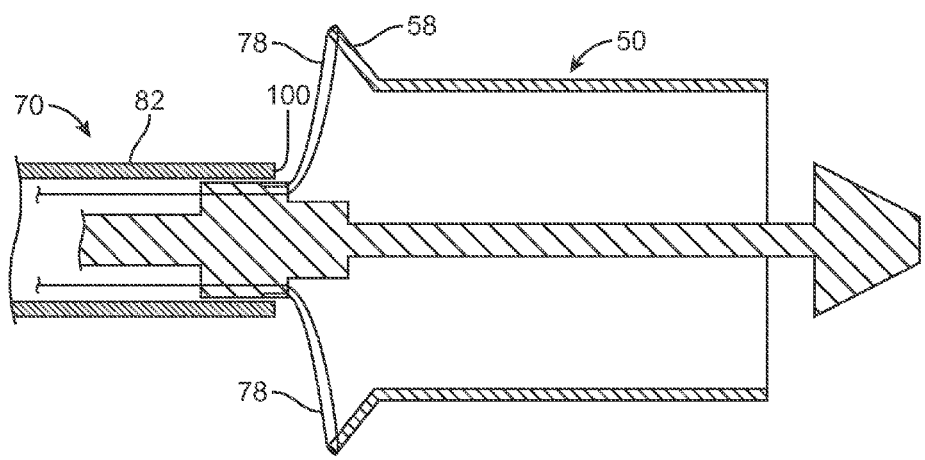

Proximal retraction of the capsule 82 continues. In the partial deployment state of FIG. 4C, the distal end 100 of the capsule 82 is now proximal to the proximal end 58 of the stent frame 50, but is distal the location of connection between the leading end 94 of each of the tethers 78 with the hub assembly 76. Thus, the tethers 78 maintain the connection of the prosthesis 90 with the delivery device 70. In this regard, the tethers 78 are held in tension (e.g., the trailing end (not shown) of each of the tethers 78 is located at the handle assembly 80 (FIGS. 3A and 3B), and coupled to a corresponding component(s) provided therewith). The tensioned tethers 78 serve to control expansion of the proximal end 58. More particularly, were the tethers 78 not present, the stent frame 50, and in particular the proximal end 58, would freely self-expand to the normal, expanded condition shown in FIG. 2. The tensioned tethers 78 prevent this self-expansion from rapidly occurring. Instead, tension in the tethers 78 is slowly released, allowing the proximal end 58 to more slowly transition toward the normal, expanded condition, as generally reflected in FIG. 4D. As described below, the handle assembly 80 optionally includes one or more mechanisms that allow a user to control tension in the tethers 78.

Figure 4E:
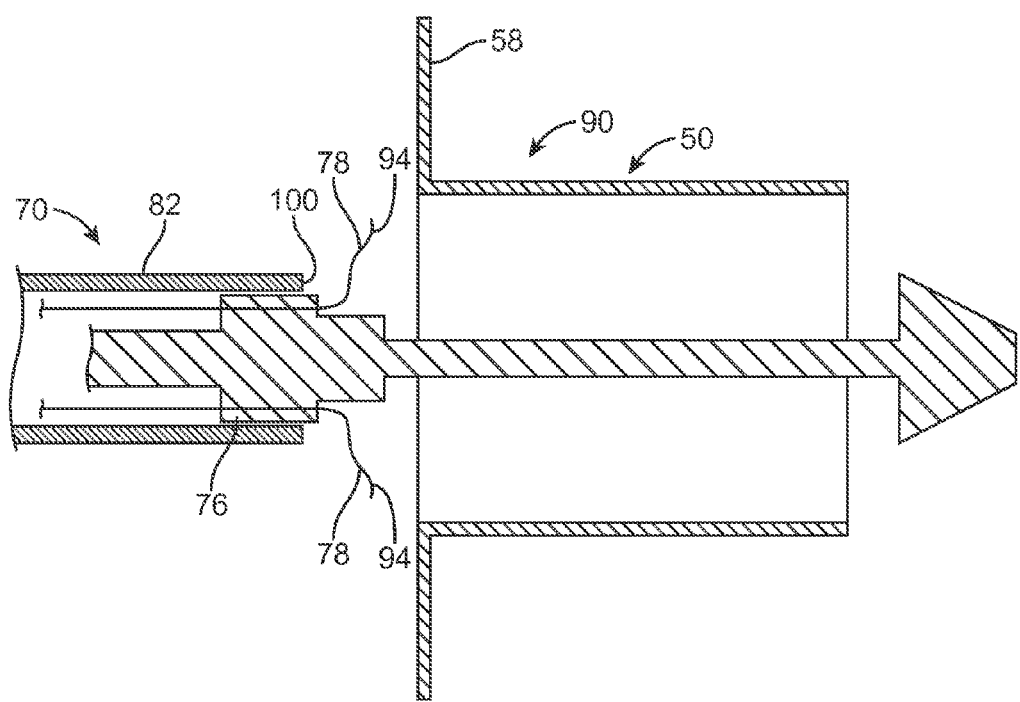

Once tension in the tethers 78 has been sufficiently lessened to permit the proximal end 58 to self-expand to the normal, expanded condition, the capsule 82 is further proximally retracted, locating the distal end 100 proximal the leading end 94 of each of the tethers 78. As shown in FIG. 4E, the tethers 78 are now no longer captured relative to the hub assembly 76, and can be removed from engagement with the stent frame 50 by, for example, proximally withdrawing the tethers 78 through the delivery device 70. Alternatively, the delivery device 70 can be configured to effectuate release of the tethers 78 from the hub assembly 76 apart from movement of the capsule 82 as described below. Regardless, with embodiments in which the tethers 78 remain robustly connected with the stent frame 50, as the stent frame 50 is allowed to expand (e.g., the looped connection described above) at any point prior to release of the leading end 94, the tethers 78 can be manipulated to perform a recapture procedure. For example, tension in the tethers 78 can be increased, causing the proximal end 58 to re-collapse or compress (e.g., transition from the expanded condition of FIG. 4D to or toward the compressed condition of FIG. 4C). Once the proximal end 58 is re-collapsed, an entirety of the stent frame 50 can more easily be compressed and recaptured relative to the delivery device 70, for example within a separate recapture sheath (not shown) slidably advanced over the capsule 82 (e.g., the delivery device 70 can be retracted relative to the recapture sheath to bring the stent frame 50 within the recapture sheath or the recapture sheath can be distally advanced over the stent frame 50) or by advancing the capsule 82 over the stent frame 50. Regardless, in the full deployment state of FIG. 4E, the stented prosthetic heart valve 90 is fully released from the delivery device 70.

Figure 5A:
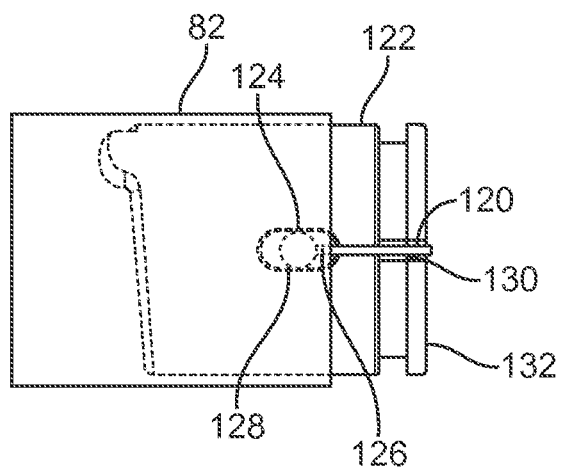
FIG. 5A is a simplified side view of valve retainer and tether components useful with delivery devices of the present disclosure and in a captured arrangement.

The hub assembly component(s) and/or the tethers 78 can assume a variety of forms that facilitate temporary coupling there between pursuant to the above descriptions. For example, FIG. 5A illustrates one embodiment of a tether 120 and a valve retainer 122 (that can be provided with the hub assembly 76 of FIG. 3A) useful with delivery devices of the present disclosure. The tether 120 forms or provides a ball 124 at a leading end 126 thereof. The valve retainer 122 forms or defines a retention hole 128 and a guide slot 130 extending from the hole 128 to a distal end 132 of the valve retainer 122. The ball 124 can be generated in a variety of manners. For example, where the tether 120 is a conventional suture, the ball 124 can be a knot formed in the suture, or can be formed by melting the leading end 126. In other embodiments, the ball 124 is a separately-formed body that is attached (e.g., adhesive, weld, etc.) to the tether 120. Regardless, the retention hole 128 is sized to selectively receive the ball 124, and the guide slot 130 is sized to accommodate a thickness of the tether 120. As a point of reference, with embodiments including two or more of the tethers 120, the valve retainer 122 will form a corresponding number of the capture retention holes 128/guide slots 130.

Figure 5B:
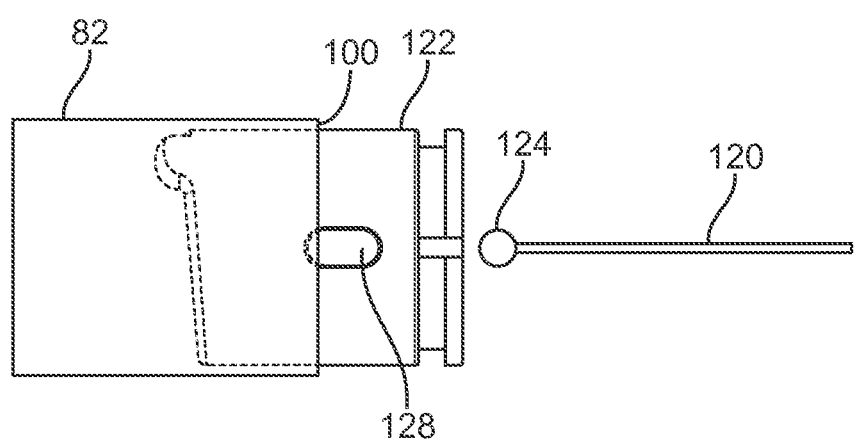
FIG. 5B is a side view of the components of FIG. 5A and in a released state.

In the assembled arrangement of FIG. 5A, the capsule 82 secures the ball 124 within the retention hole 128. With proximal retraction of the capsule 82 to the arrangement of FIG. 5B, the distal end 100 of the capsule 82 is moved proximal the ball 124, allowing the tether 120 to release from the valve retainer 122 as described above.

In some embodiments, the valve retainer 122 can incorporate various features that assist in loading the prosthesis (not shown) to the delivery device, and in particular connecting the tether(s) 120 with the valve retainer 122. As a point of reference, where the particular delivery device incorporates a plurality of the tethers 120, it can be difficult to loop the tethers 120 through the stent frame and then hold all of the tethers 120 in place relative to the valve retainer 122 while simultaneously locating the assembly within the capsule 82. With this in mind, in some embodiments, the guide slot 130 is optionally provided and is formed to a width approximating a diameter of the tether 120. With this construction, the tether 120 will be frictionally held within the corresponding slot 130 during loading. Notably, however, the frictional force or interface between the tether 120 and the valve retainer 122 at the slot 130 is significantly less than the expected radially-outward force applied onto the tether 120 by the stent frame (not shown) in self-expanding from the compressed condition to the normal, expanded condition. Thus, the tether 120 will readily disengage from the slot 130 during deployment.

Figure 5C:
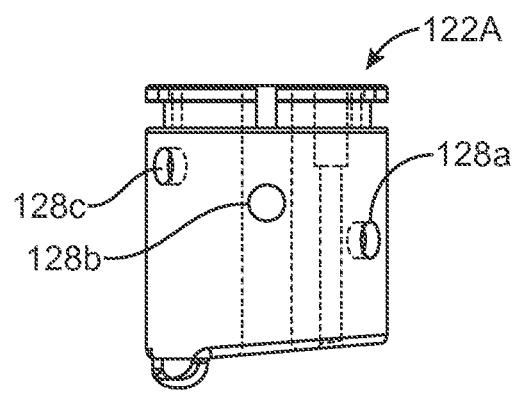
FIG. 5C is a side view of another valve retainer useful with delivery devices of the present disclosure.

FIG. 5C illustrates another embodiment valve retainer 122A useful with delivery devices of the present disclosure, and is akin to the valve retainer 122 (FIG. 5A) described above. As shown, the valve retainer 122A forms a plurality of the retention holes 128a-128c for retaining a corresponding number of the tethers (not shown). The retention holes 128a-128c are offset from one another in a spiral configuration. With this construction, loading of the prosthesis (not shown) can include looping a first tether (not shown) through the stent frame and locating the corresponding leading end within the first retention hole 128a. The capsule (not shown) is then distally advanced over the first retention hole 128a to capture the first tether. However, the remaining retention holes 128b, 128c remain uncovered. The process is repeated to sequentially secure second and third tethers (not shown) to the second and third retention holes 128b, 128c.

Figure 5D:
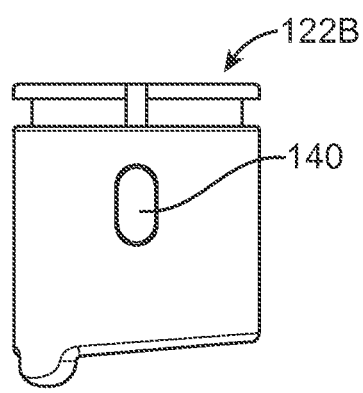
FIG. 5D is a side view of another valve retainer useful with delivery devices of the present disclosure.

FIG. 5D illustrates another embodiment valve retainer 122B useful with delivery devices of the present disclosure, and is akin to the valve retainer 122 (FIG. 5A) described above. As shown, the valve retainer 122B forms or defines a plurality of enlarged retention holes 140 (one of which is shown in FIG. 5D). As compared to dimensions of the retention hole 128 of FIG. 5A, the enlarged retention holes 140 have an elevated length, but are sized (width) to house the tether leading end (not show, but for example the ball 124 of FIG. 5A). During loading, the capsule (not shown) is advanced partially over the valve retainer 122B so as to cover a proximal segment of each the retention holes 140. A small gap remains between the capsule and the distal end of the each of the retention holes. The tethers (not shown) are then looped through the stent frame (not shown), and the corresponding leading end forced or pushed through the gap and into the covered, proximal segment of the corresponding retention hole 140.

The valve retainers or other hub assembly components of the present disclosure can incorporate other features conducive to selectively retaining a leading end of the tether(s). In other embodiments of the present disclosure, the delivery device can include one or more features that promote release of the tether leading end from the hub assembly.

Figure 6C:
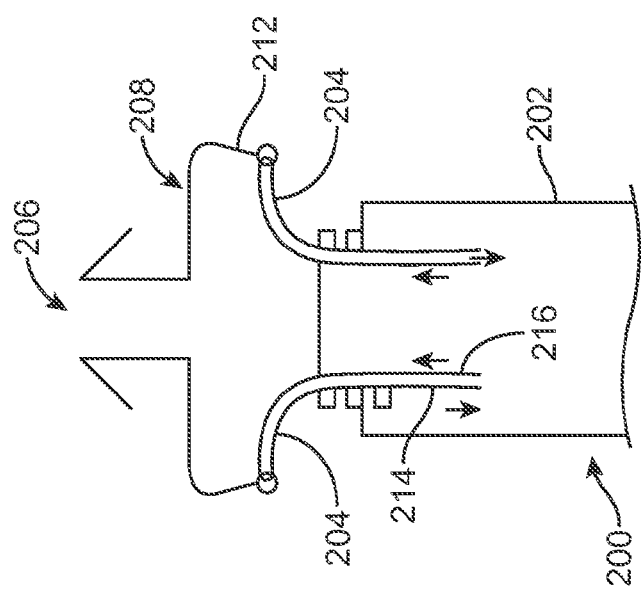
FIGS. 6A-6C are simplified side views illustrating operation of another embodiment delivery device in accordance with principles of the present disclosure in conjunction with a prosthetic heart valve stent frame.
Figure 6B:
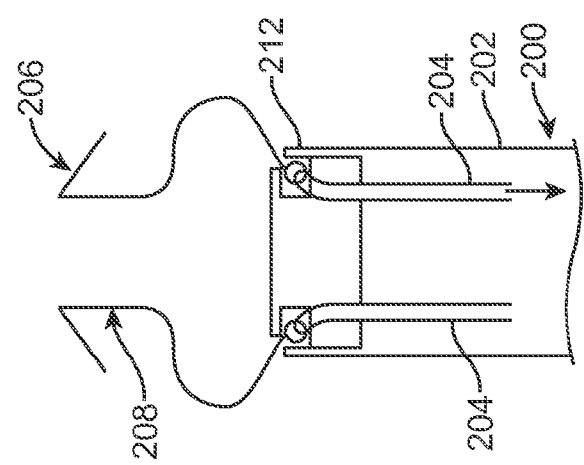
Figure 6A:
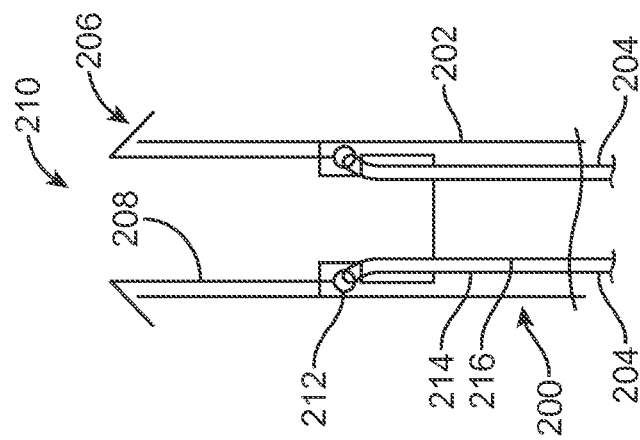

While several of embodiments of the present disclosure couple a leading end of the tether(s) to the retainer, in other constructions the tether(s) is not directly connected to the retainer. For example, FIGS. 6A-6C illustrate, in simplified form, portions of another delivery device 200 in accordance with principles of the present disclosure and including a delivery sheath assembly 202 and a plurality of tethers 204. The delivery device 200 is shown relative to a prosthetic heart valve 206 having a stent frame 208, with the delivery device 200 and the prosthesis 206 combining to provide a system 210 in accordance with principles of the present disclosure. In the delivery state of FIG. 6A, each of the tethers 204 is looped through a proximal portion 212 of the stent frame 208 such that the tethers 204 can be viewed as defining opposing, first and second tether segments 214, 216. The tether segments 214, 216 are routed proximally through the delivery sheath assembly 202, for example through passageways in an inner shaft assembly (not shown), to a handle assembly (not shown) of the delivery device 200.

In the partial deployment state of FIG. 6B, the delivery sheath assembly 202 has been proximally retracted from over the prosthetic heart valve 206, allowing regions of the stent frame 208 to self-expand toward the natural, expanded condition. The tethers 204 remain connected to the stent frame 208 and are under tension, thus impeding rapid, complete expansion of the proximal portion 212. As tension in the tethers 204 is released, the proximal portion 212 is allowed to self-expand toward the normal condition in a controlled fashion, as represented by FIG. 6C. Once the stent frame 208 has completely expanded, the tethers 204 can be removed, for example by pulling on either the first or second tether segment 214, 216 of each of the tethers 204. At any point prior to release of the tethers 204 from the stent frame 208, tension in the tethers 204 can be increased to at least partially re-collapse the proximal portion 212 as part of an optional recapture operation.

Figure 7A:
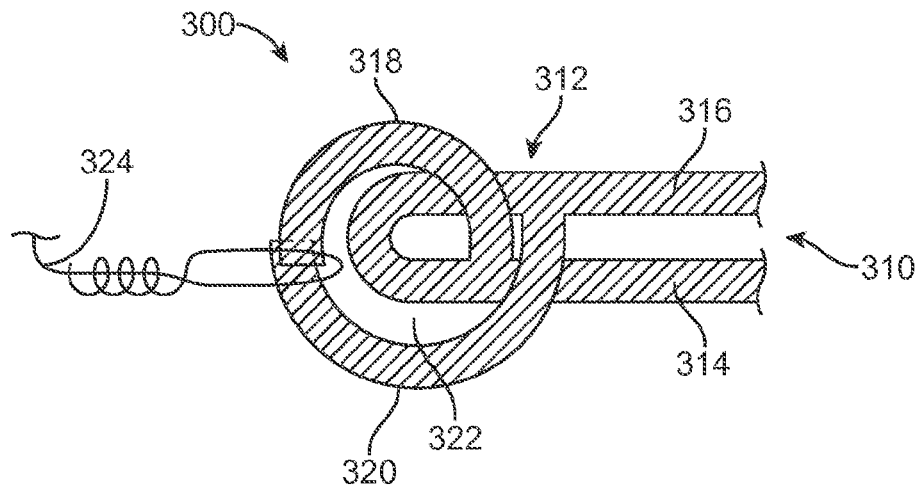
FIG. 7A is a side view of a portion of another embodiment prosthetic heart valve stent frame useful with delivery devices of the present disclosure in a compressed condition, along with a tether.
Figure 7B:
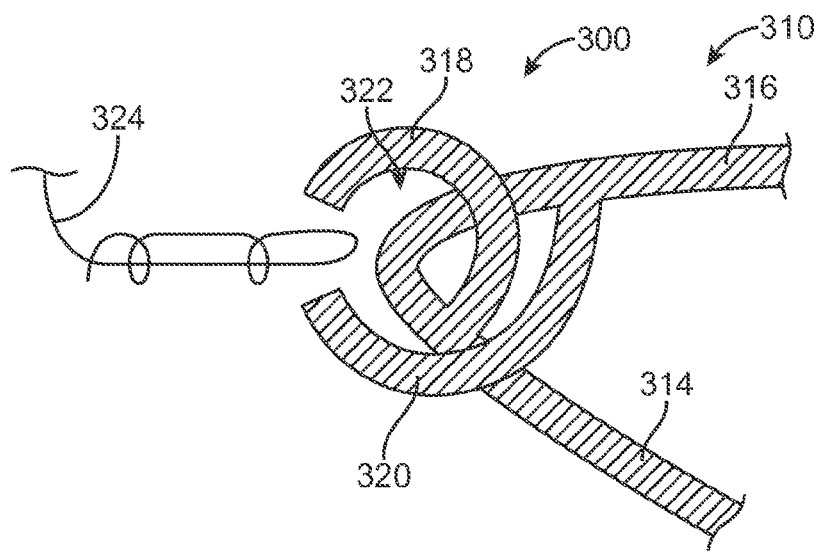
FIG. 7B is a simplified side view of the arrangement of FIG. 23A, with the stent frame in a normal, expanded condition.

While some embodiments described above generally entail looped-type connection of the tether(s) relative to the corresponding prosthetic heart valve stent frame, in other constructions, the tether can be more robustly connected to, or terminate at, the stent frame. Self-releasing, temporary engagement between the tether leading end and the stent frame can be provided in a variety of manners. One or more tethers can be temporarily connected to the corresponding prosthetic heart valve stent frame in a looped, twisted or wrapped manner. Further, the stent frame can incorporate one or more additional features that better ensure complete unwinding of the tether upon full deployment of the stent frame. For example, portions of another system 300 in accordance with principles of the present disclosure are shown in simplified form in FIGS. 7A and 7B. The system 300 includes a prosthetic heart valve stent frame 310 useful with delivery devices of the present disclosure. The stent frame 310 includes a conventional cell structure 312 defined, at least in part, by opposing, first and second strut segments 314, 316. A first barb 318 extends from the first strut segment 314, and a second barb 320 extends from the second strut segment 316. The barbs 318, 320 are sized and shaped such that in the compressed condition of the stent frame 310 reflected by FIG. 7A, the barbs 318, 320 cross over one another to generate a capture zone 322. In the compressed condition of FIG. 7A, the capture zone 322 is "closed," completely bounded, at least in the proximal direction, by the barbs 318, 320. The barbs 318, 320 are further configured such that in the normal, expanded condition of the stent frame 310, the capture zone 322 is open as shown in FIG. 7B.

With the above construction, with the stent frame 310 in the compressed condition, a tether 324 can be wound or twisted about the stent frame 310 and temporarily secured thereto via the closed capture zone 322. This connection is shown in FIG. 7A. As the tether 324 allows the stent frame 310 to slowly self-expand toward the normal, expanded condition as described above, the barbs 318, 320 spatially move relative to one another to "open" the capture zone 322. As shown in FIG. 7B, then, upon full deployment of the stent frame 310, the tether 324 is released from the capture zone 322 and freely unwinds from the stent frame 310.

Figure 8A:
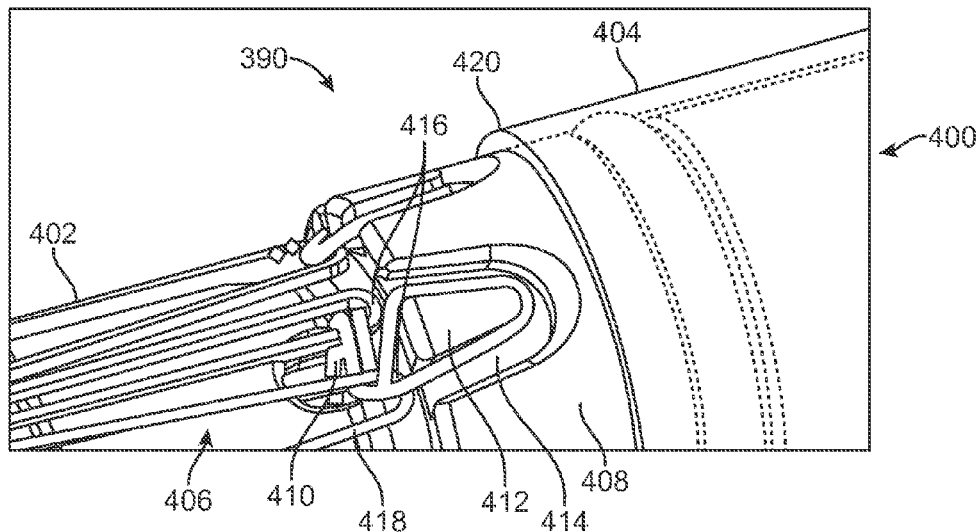
FIG. 8A is a perspective view of a portion of another embodiment delivery device in accordance with principles of the present disclosure, along with a portion of prosthetic heart valve stent frame in a compressed condition.
Figure 8B:
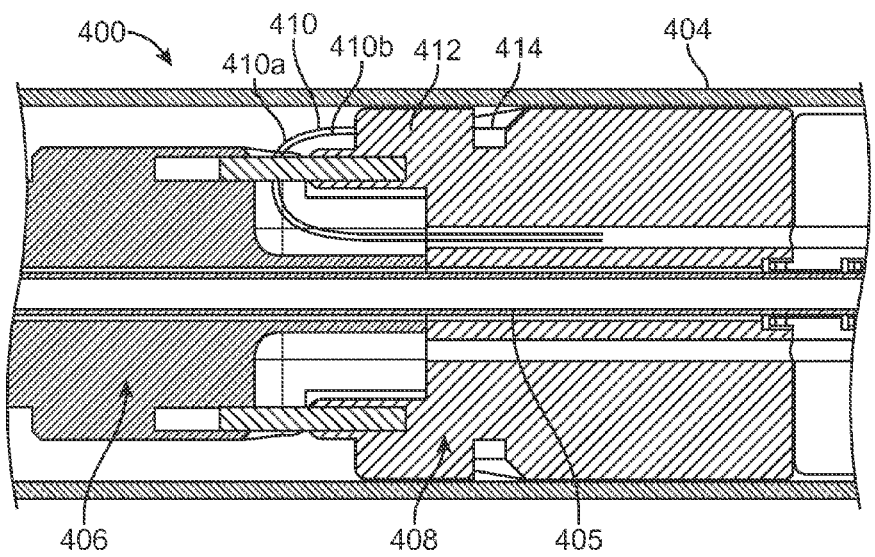
FIG. 8B is a cross-sectional view of a portion of the delivery device of FIG. 8A.

Connection between the tether(s), prosthetic heart valve stent frame, and other components of the delivery device can assume a variety forms in accordance with the present disclosure. For example, FIG. 8A illustrates a portion of another system 390, including another embodiment delivery device 400 and a prosthetic heart valve stent frame 402. The delivery device 400 includes a delivery sheath assembly 404, an inner shaft assembly 405 (primarily hidden in FIG. 8A, but shown in FIGS. 8B and 9A), a hub assembly including a valve support 406 and a valve retainer 408, and a plurality of tethers 410. The valve retainer 408 is attached to, or formed by, the inner shaft assembly 405, and forms a plurality of posts 412 (one of which is visible in FIG. 8A). A groove 414 is defined about each of the posts 412, and is sized to permit winding of a corresponding one of the tethers 410 around the post 412. In the delivery state generally reflected by FIG. 8A, each of the tethers 410 extends from the corresponding post 412 and is looped through the stent frame 402. For example, relative to the tether 410 identified in FIG. 8A, the tether 410 is looped through or around two crowns 416 formed at a proximal portion 418 of the stent frame 402. FIG. 8B is a simplified cross-sectional view of a portion of the delivery device 400, and reflects that the tether 410 is looped about the corresponding post 412, effectively defining first and second tether segments 410a, 410b extending from the post 412. The tether segments 410a, 410b are connected to the stent frame 402 (FIG. 8A) and then routed proximally to and optionally through at least the valve retainer 408. The tether segments 410a, 410b can extend to a handle assembly (not shown) of the delivery device 400 or can be connected to another component of the delivery device 400 adapted to facilitate user control over a tension in the tether 410.

With the above construction in mind and returning to FIG. 8A, the delivery sheath assembly 404 serves to retain the tethers 410 relative to the corresponding post 412. As a point of reference, FIG. 8A illustrates a distal end 420 of the delivery sheath assembly 404 as being proximal the posts 412 for ease of illustration. In the delivery state of the delivery device 400, however, the distal end 420 is distal the posts 412 so as to maintain engagement of the tethers 410 with the posts 412. Further, as with previous embodiments, in the delivery state the distal end 420 is located distal the stent frame 402 to constrain the stent frame 402 to the compressed condition.

Figure 9A:
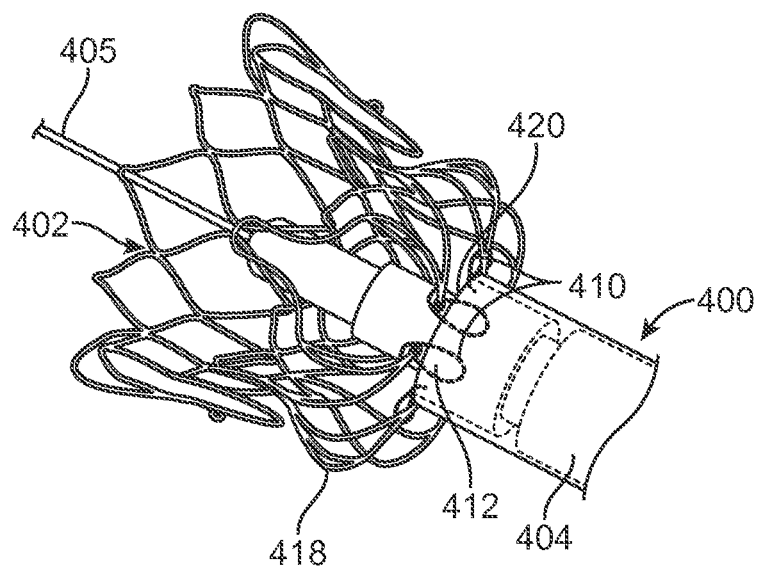
FIG. 9A is a perspective view a portion of the assembly of FIG. 8A in a partial deployment state.
Figure 9B:
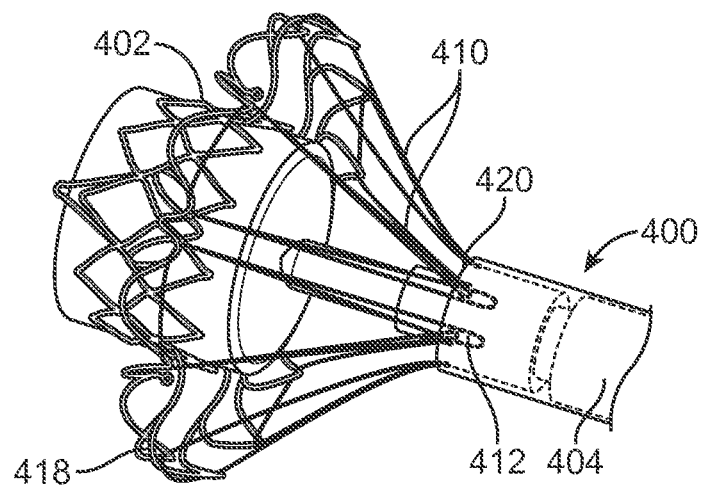
FIG. 9B is a perspective view of the arrangement of FIG. 9A and in a subsequent stage of partial deployment.

FIG. 9A depicts the delivery device 400 in the initial stages of a partial deployment state. The distal end 420 of the delivery sheath assembly 404 is proximal a significant portion of the stent frame 402, such that stent frame 402 self-expands toward the normal, expanded condition. However, the distal end 420 remains distal each of the tether 410/post 412 interfaces such that each of the tethers 410 remains connected to the corresponding stent frame 402. Tension in the tethers 410 resists rapid expansion of the proximal portion 418. As reflected by FIG. 9B, the tethers 410 allow the proximal portion 418 to slowly attain the normal, expanded condition. The tethers 410 remain connected to the corresponding posts 412 within the delivery sheath assembly 404. Under circumstances where a user desires to recapture the stent frame 402 for re-deployment at another anatomical location or removal from the patient, tension in the tethers 410 can be increased to cause the proximal portion 418 to at least partially re-collapse or compress back toward the compressed condition. This action, in turn, facilitates recapture of an entirety of the stent frame 402 within a separate recapture sheath (not shown), for example by advancing the recapture sheath over the delivery sheath assembly 404; the delivery system 390 can then be retracted to bring the stent frame 402 into the recapture sheath, or the recapture sheath can be advanced over the partially collapsed stent frame 402. In other recapture operations, the partially collapsed stent frame 402 can be reinserted back within the delivery sheath assembly 404.

Figure 10A:
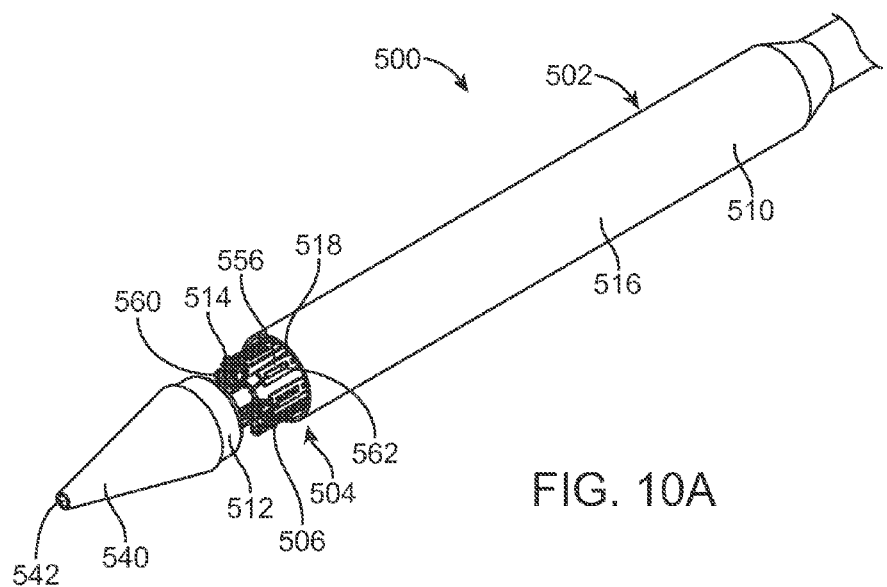
FIG. 10A is a perspective view of another embodiment system in accordance with principles of the present disclosure, including a delivery device loaded with a prosthetic heart valve stent frame and in a delivery state.
Figure 10B:
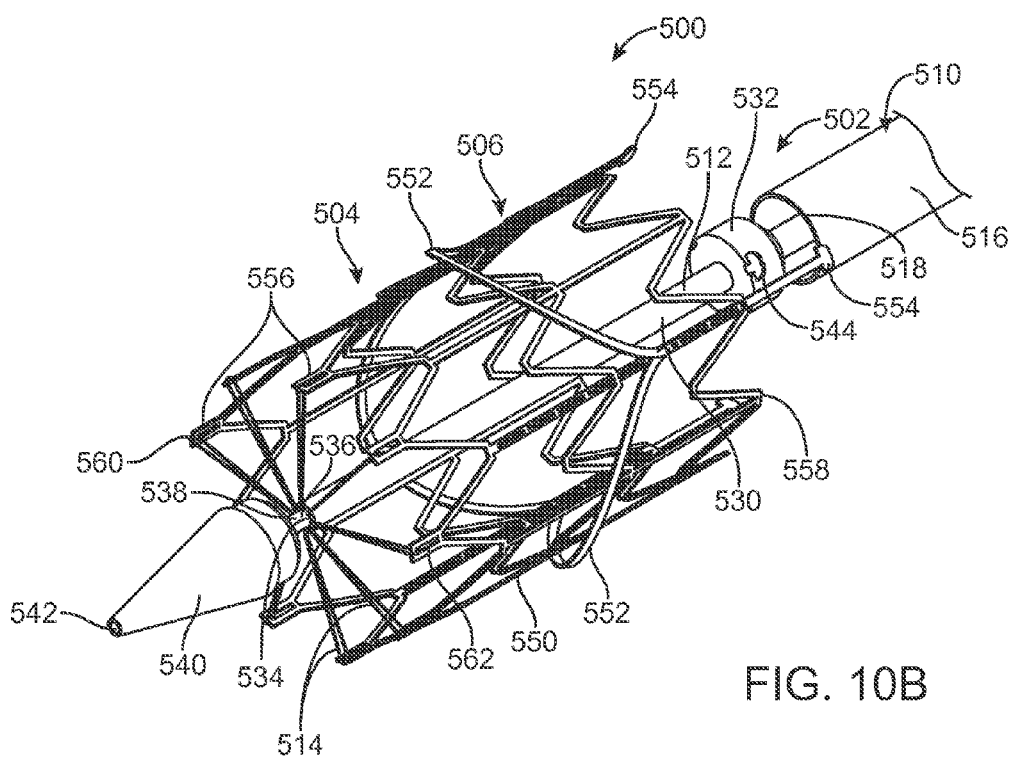
FIG. 10B is a perspective view of the system of FIG. 10A in a partial deployment state and immediately prior to full deployment of the stent frame.

While several of the above embodiments connect the tether(s) at or adjacent a proximal portion of the corresponding prosthetic heart valve stent frame, in other constructions, a more distal connection can be provided. For example, portions of another embodiment system 500 for performing a therapeutic procedure on a patient's heart are shown in FIGS. 10A-10B. The system 500 includes a delivery device 502 and a prosthetic heart valve 504 (referenced generally). As a point of reference, only a stent frame assembly 506 of the prosthetic heart valve 504 is illustrated in several of the views. FIG. 10A reflects the stent frame assembly 506 loaded to the delivery device 502 and is indicative of a delivery state. FIG. 10B depicts the stent frame assembly 506 partially deployed from the delivery device 502 (and alternatively can be viewed as an initial stage of loading the stent frame assembly 506 to the delivery device 502).

The delivery device 502 includes an outer sheath assembly 510, an inner shaft assembly 512, and a plurality of tethers 514. The delivery sheath assembly 510 includes or forms a capsule 516 terminating at a distal end 518. As with previous embodiments, the delivery sheath assembly 510 is coaxially received over the inner shaft assembly 512, and is longitudinally slidable relative to the inner shaft assembly 512.

A identified in FIG. 10B, the inner shaft assembly 512 includes a primary shaft 530 and carries a valve retainer (or other hub assembly component) 532. The primary shaft 530 forms or defines a plurality of side lumens 534 (referenced generally) sized to receive respective ones of the tethers 514. An optional central guide lumen 536 (referenced generally) is also provided, and through which an optional secondary shaft 538 is disposed. The secondary shaft 538 extends distally from the primary shaft 530, and is attached to or forms a dilator tip 540. In some embodiments, the dilator tip 540 and the secondary shaft 538 define a common guidewire lumen 542.

The valve retainer 532 can assume a variety of forms, and is attached to the primary shaft 530. In general terms, the valve retainer 532 incorporates one or more features commensurate with components of stent frame assembly 506 that facilitate mounting of the stent frame assembly 506 to the inner shaft assembly 512. For example, and as best shown in FIG. 10B, the valve retainer 532 can form one or more slots 544 sized and shaped to receive a corresponding component of the stent frame assembly 506.

The plurality of tethers 514 can assume any of the forms described above (e.g., threads, sutures, thin wires, etc.), and are slidably disposed within respective ones of the side lumens 534. In some embodiments, the primary shaft 530 routes each of the tethers 514 proximally to a handle assembly (not shown) provided with the delivery device 502, with the handle assembly, in turn, including one or more mechanisms configured to provide user control over ends of each of the tethers 514 and/or tension within the tethers 514.

Figure 10C:
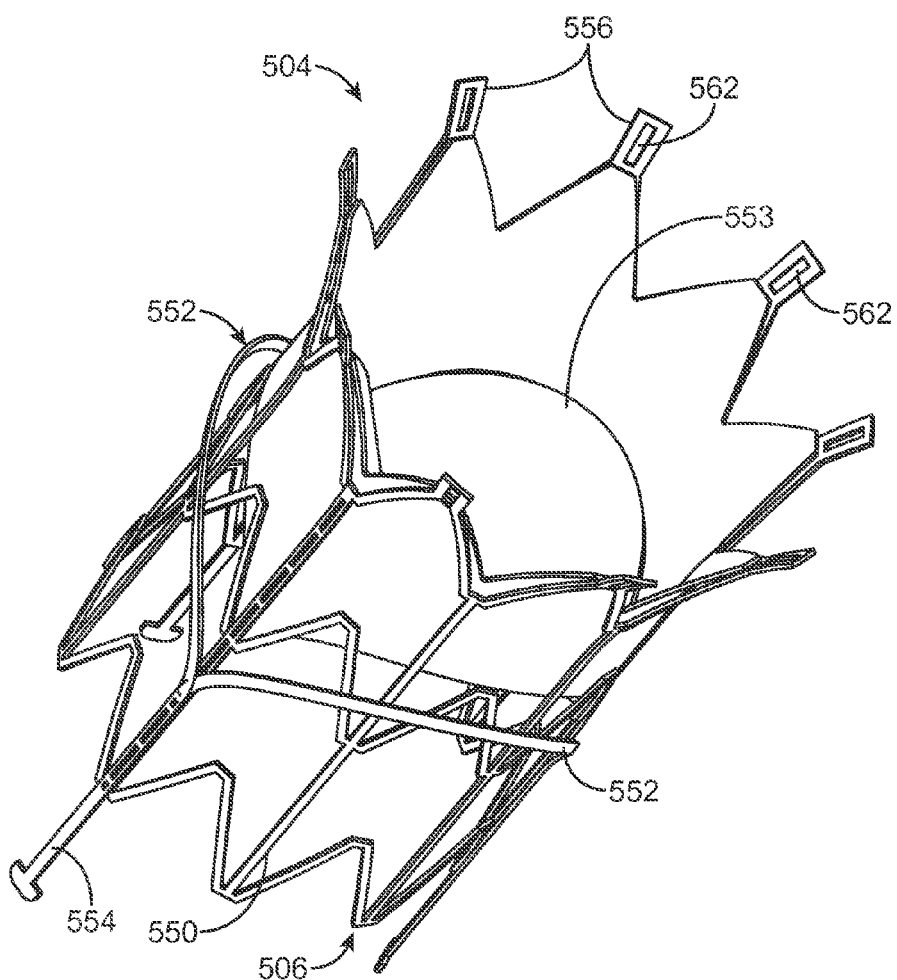
FIG. 10C is a perspective view of the prosthetic heart valve of FIG. 10A.

With additional reference to FIG. 10C, the stent frame assembly 506 can assume a variety of forms and some embodiments includes a stent frame 550 and a plurality of support arms 552. The stent frame 550 carries a valve structure 553 provided with the prosthetic heart valve 504, and is configured to self-expand from a compressed condition (such as the compressed condition of FIG. 10A) to the normal, expanded condition (of FIG. 10C). The stent frame 550 further defines various features that promote connection with the delivery device 502 and/or the valve structure 553, as well as desired interface with native anatomy of the heart valve being treated. For example, the stent frame 550 can form or define posts 554 and crowns 556. Relative to an orientation of the stent frame assembly 506 upon mounting to the delivery device 502, the posts 554 are located at a proximal end 558 of the stent frame 550, whereas the crowns 556 are at a distal end 560. The crowns 556 can have various formats, and in some embodiments are akin to an eyelet that defines an aperture 562 (identified for one of the crowns 556 in FIGS. 10A and 10B).

The support arms 552 are optionally provided with the stent frame assembly 506, extending outwardly from the stent frame 550. The support arms 552 can each have generally curved shape shown, and are configured to interface with structures of the native valve anatomy, such as the native leaflets.

Figure 10D:
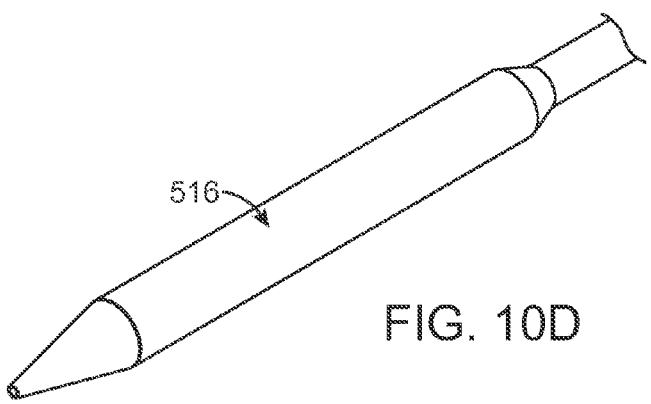
FIG. 10D is a perspective view of the system of FIG. 10A and in a delivery state.

Assembly of the system 500 includes locating the stent frame assembly 506 over the inner shaft assembly 512, and then connecting each of the tethers 514 to the distal end 560 of the stent frame 550. For example, each of the tethers 514 is looped through a respective one of the crowns 556 (via the corresponding aperture 562). The tethers 514 are routed through corresponding ones of the side lumens 534 proximally to the handle assembly (not shown). The stent frame assembly 506 is crimped or compressed onto the inner shaft assembly 512. For example, the posts 554 can be located within respective ones of the slots 544 provided with the valve retainer 532. In the compressed condition, the stent frame assembly 506 is loaded within the capsule 516 as generally reflected in FIG. 10A and fully shown in FIG. 10D. Any slack in the tethers 514 is removed, and the tethers 514 are then locked. In this held arrangement, the tethers 514 prevent or impede radial self-expansion of the distal end 560.

Figure 11A:
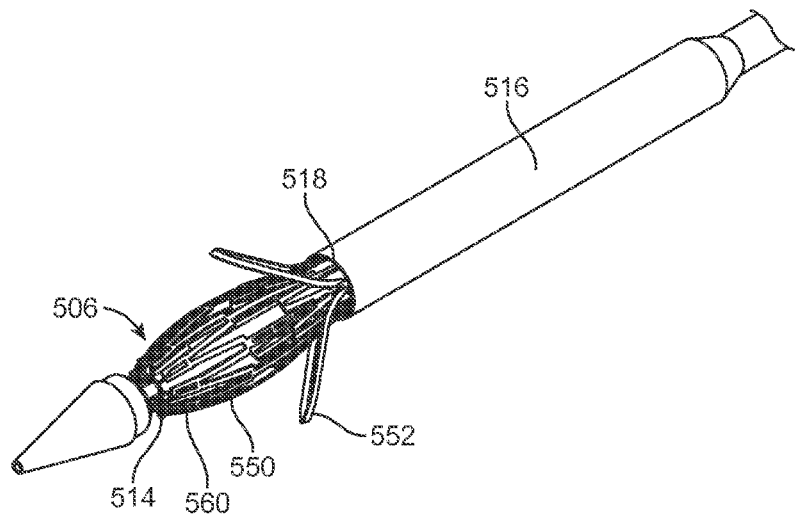
FIG. 11A is a perspective view of the system of FIG. 10A and illustrating transitioning of the system toward the arrangement of FIG. 10B.
Figure 11B:
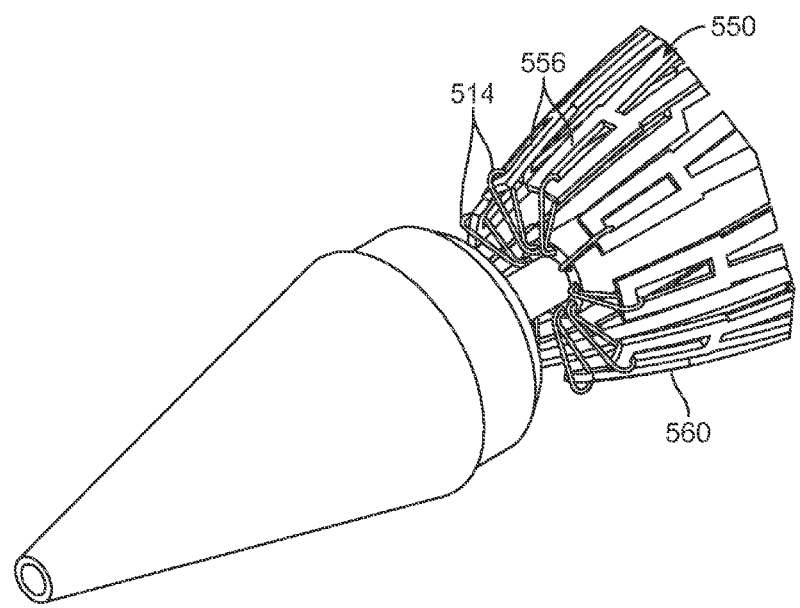
FIG. 11B is an enlarged, perspective view of a portion of FIG. 11A.

During use, the prosthetic heart valve 504 can be deployed from the delivery device 502 in a progressive fashion. For example, FIG. 11A illustrates an initial stage of deployment. The capsule 516 has been proximally retracted relative to the stent frame assembly 506, locating the distal end 518 proximal the support arms 552. As shown, once removed from the confines of capsule 516, the support arms 552 self-expand to or toward the normal, expanded condition. While a substantial portion of the stent frame 550 is also now distal the capsule 516 and thus free of the constraints presented by the capsule 516, the tethers 514 prevent or impede self-expansion of the stent frame 550, at least at the distal portion 560. As shown in greater detail in FIG. 11B, the tethers 514 remain connected to the stent frame 550 at the crowns 556. Because the tethers 514 are locked, the tethers 514 are placed in tension by the stent frame 550, and prevent overt radial expansion of the distal portion 560. While regions of the stent frame 550 proximal the distal portion 560 may experience some minor expansion, the stent frame 550 is essentially maintained in the compressed condition.

Figure 12A:
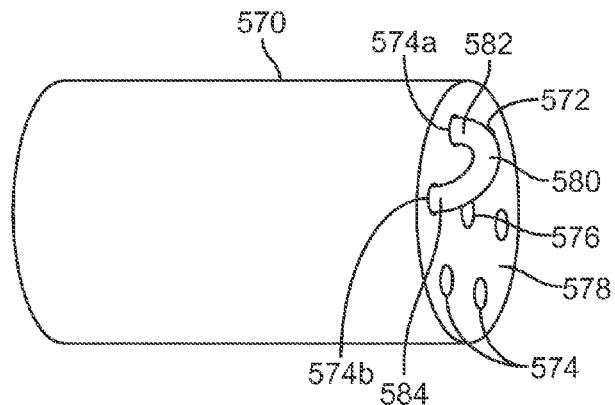
FIGS. 12A-12C are simplified perspective views of a portion of a control shaft and tether useful with the system of FIG. 11A.

When desired, tension in the tethers 514 can be progressively lessened, thereby permitting the distal portion 560 to self-expand. In some embodiments, the tethers 514 can be removed by simply pulling on one end of each of the tethers 514 (while the opposite end is unlocked). In other embodiments, the delivery device 502 can incorporate features that promote a more rapid release of the tethers 514. For example, FIG. 12A illustrates a portion of an alternative embodiment primary shaft 570 useful with the delivery device 502 (FIG. 10A) described above, along with one tether 572. The primary shaft 570 forms a plurality of side lumens 574 along with a central guide lumen 576. The tether 572 can have a more rigid instruction (e.g., a thin metal wire), and is arranged relative to a distal side 578 of the shaft 570 to define a looped end 580. Commensurate with the above descriptions, the looped end 580 is connected to a corresponding feature of the prosthetic heart valve stent frame (not shown), such as the crowns 556 (FIG. 10A). Regardless, first and second segments 582, 584 are defined as extensions from the looped end 580, and are routed through respective ones of the side lumens (labeled as 574a, 574b in FIG. 12A).

Figure 12B:
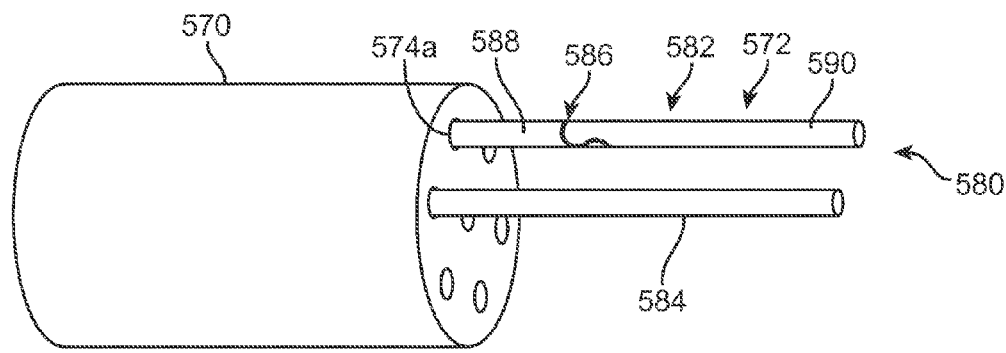
Figure 12C:
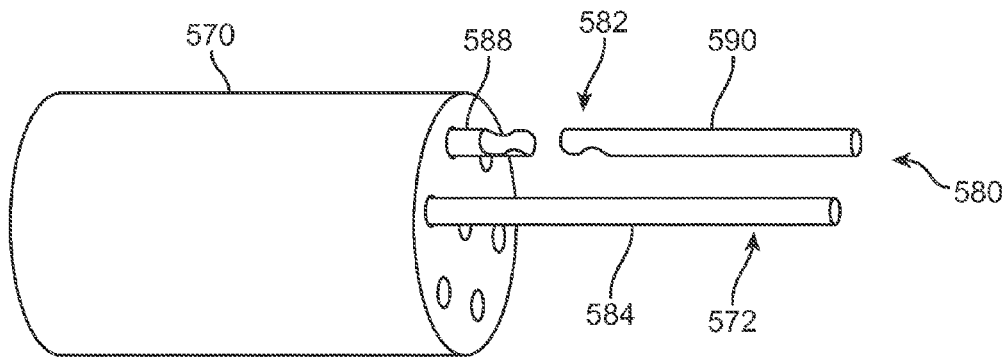

The looped end 580 of the tether 572 can be advanced in the distal direction, for example, to release tension developed in the tether 572. In the view of FIG. 12B, the looped end 580 (referenced generally) has been distally advanced from the primary shaft 570. FIG. 12B further reflects that the tether 572 forms a joint 586 along the first segment 582. The joint 586 effectively divides the first segment 582 into a proximal region 588 and a distal region 590. The proximal and distal regions 588, 590 are connected to one another at the joint 586, with a configuration of the joint 586 being such that when located within the side lumen 574a, the proximal and distal regions 588, 590 cannot separate from one another even in the presence of significant tension along the first segment 582 (i.e., so long as the joint 586 is within the primary shaft 570, the proximal and distal regions 588, 590 remain robustly connected to one another). However, once the joint 586 is distally located beyond the primary shaft 570, the distal region 590 separates from the proximal region 588 as shown in FIG. 12C. Once separated, the tether 572 can completely withdraw from the prosthetic heart valve stent frame (not shown) by proximally retracting the second segment 584 (it being recalled that the distal region 590 is connected to the second segment 584 at the looped end 580 (referenced generally)).

Figure 13A:
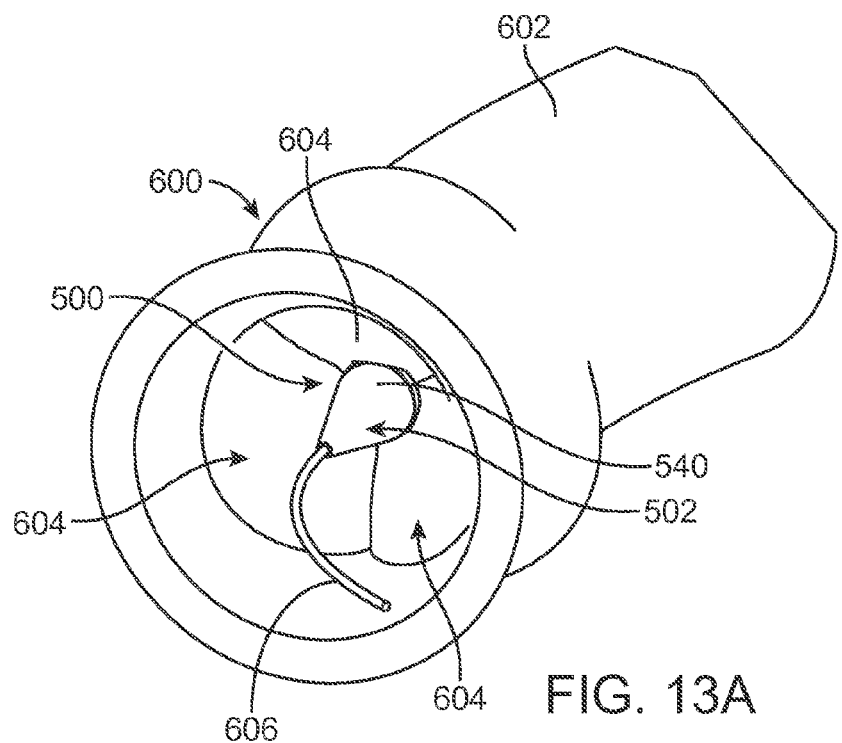
FIGS. 13A-15D illustrate use of the system of FIG. 11A, including operation of the delivery device in deploying the stent frame to a native mitral valve.
Figure 13B:
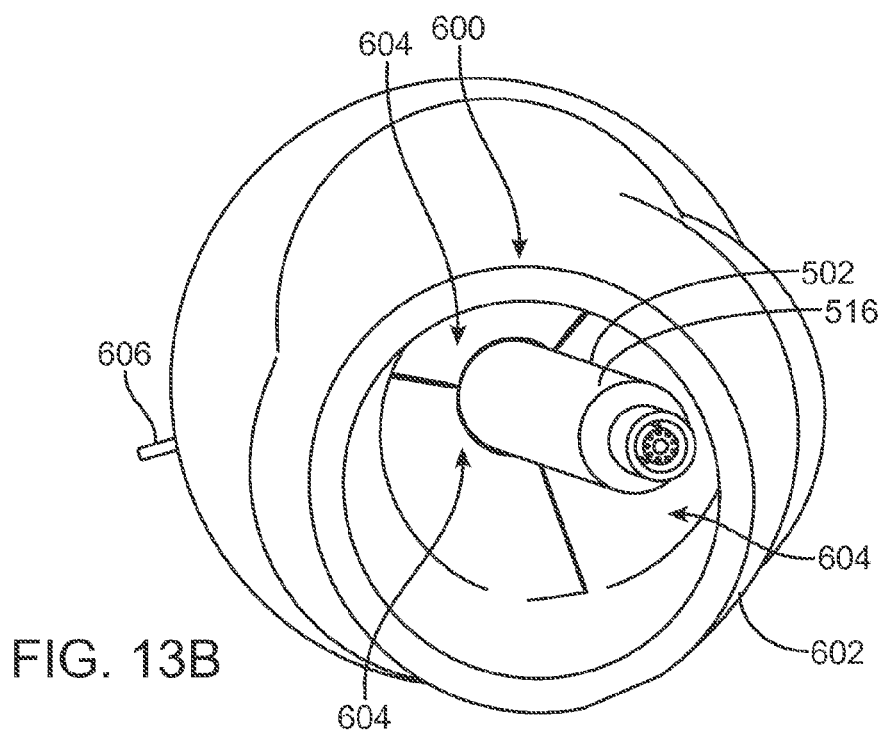

Returning to FIG. 10A, the system 500 can be configured to repair any heart valve, and in some embodiments is useful with the aortic valve. With this in mind, FIG. 13A provides a simplified representation of an aortic valve 600 taken from the vantage point of the left ventricle. An ascending portion 602 of the aorta is also identified. The aortic valve 600 generally includes three leaflets 604. The system 500 (referenced generally) is delivered through the ascending aorta 602 in various manners, such as a transfemoral delivery approach. A guide wire 606 can be employed to track the delivery device 502 to the aortic valve 600. The dilator tip 540 is positioned slightly beyond the valve 600 as shown. The location of the delivery device 502 relative to the aortic valve 600 of FIG. 13A is further represented from the vantage point of the ascending aorta 602 in FIG. 13B. At this initial stage of the procedure, the capsule 516 remains completely over the prosthetic heart valve (hidden in the view of FIG. 13B), maintaining the stent frame assembly 506 (hidden) in the compressed condition.

Figure 14A:
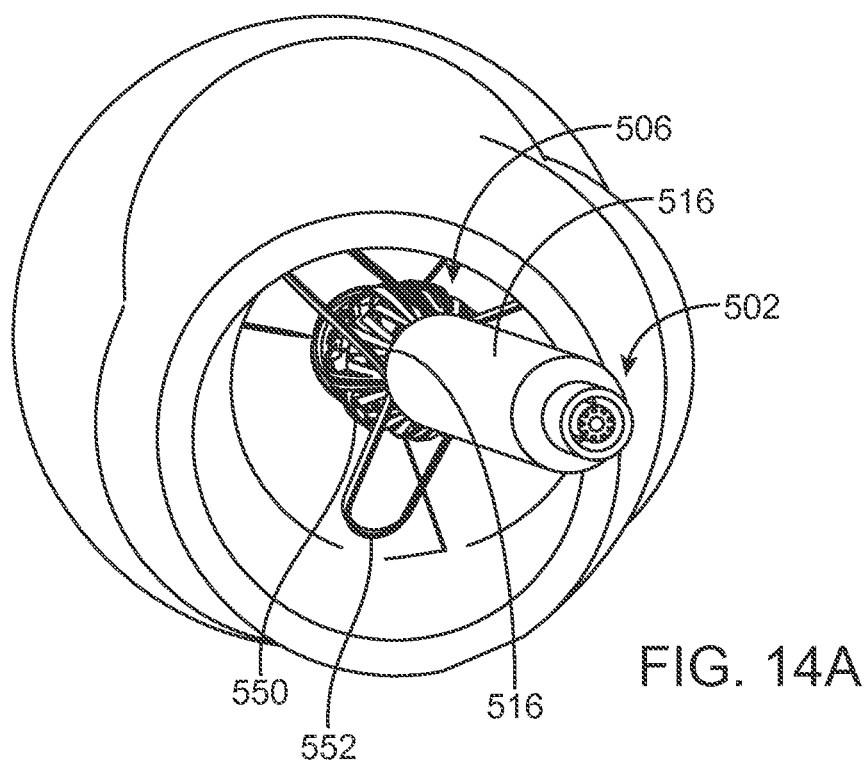
Figure 14B:
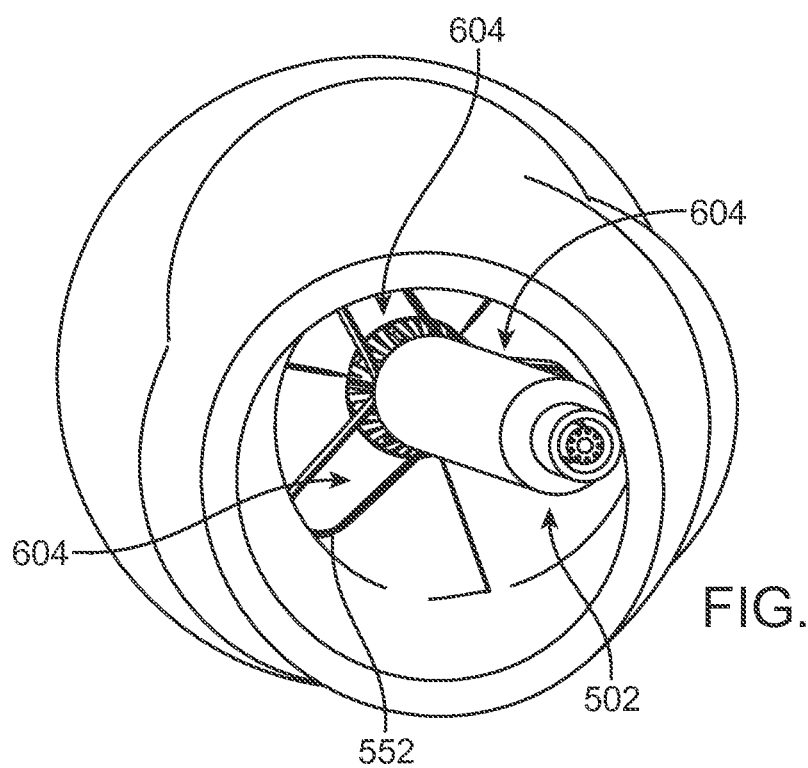

The capsule 516 is then proximally retracted relative to the stent frame assembly 506 as shown in FIG. 14A. More particularly, the capsule 516 is refracted a sufficient distance to expose the support arms 552, thus allowing the support arms 552 to self-expand as shown. As a point of reference, the arrangement of FIG. 14A is akin to that of FIG. 11A whereby the distal end 518 of the capsule 516 remains over the proximal portion 558 of the stent frame 550, such that the proximal portion 558 remains compressed and connected to delivery device 502. Further, the tethers 514 (FIG. 11A) are placed in tension, preventing the distal portion 560 (FIG. 11A) of the stent frame 550 from self-expanding. The delivery device 502 is then distally advanced until the support arms 552 engage the leaflets 604 as shown in FIG. 14B.

Figure 15A:
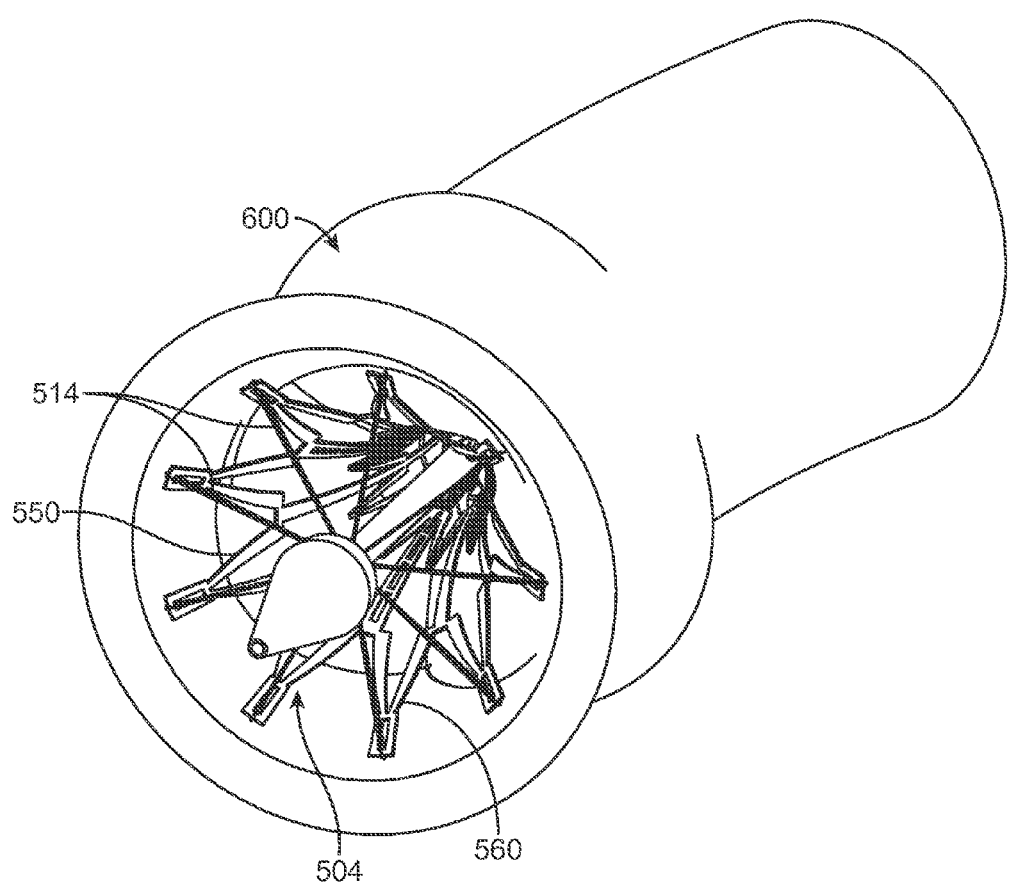

Subsequently, tension in the tethers 514 is progressively lessened, allowing the distal portion 560 of the stent frame 550 to radially self-expand as shown in FIG. 15A. FIG. 15B provides a sectional view of the aortic valve 600 with the system 500 in the partial deployment state of FIG. 15A. Where desired, the distal portion 560 can be re-collapsed by pulling on the tethers 514, permitting repositioning of the prosthetic heart valve 504 relative to the aortic valve 600.

Figure 15C:
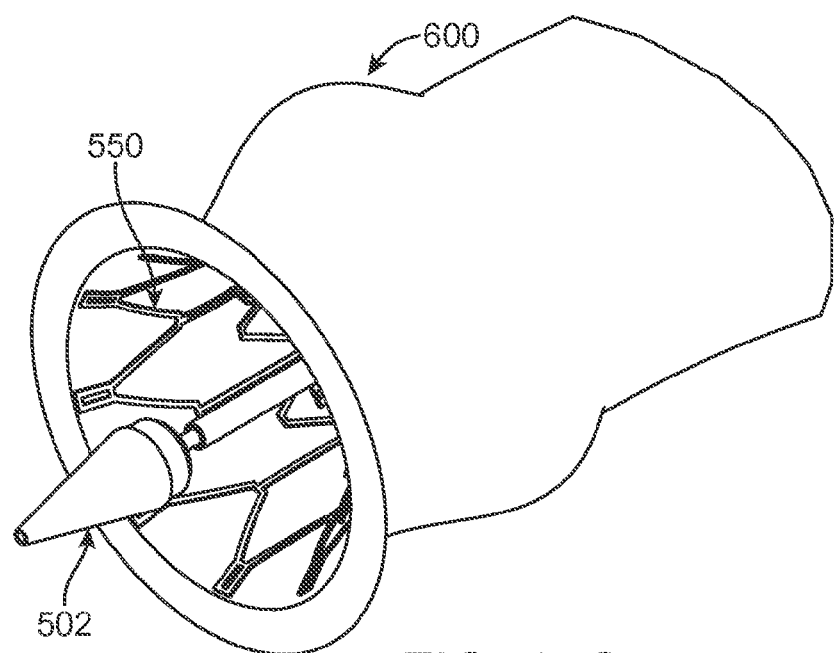
Figure 15D:
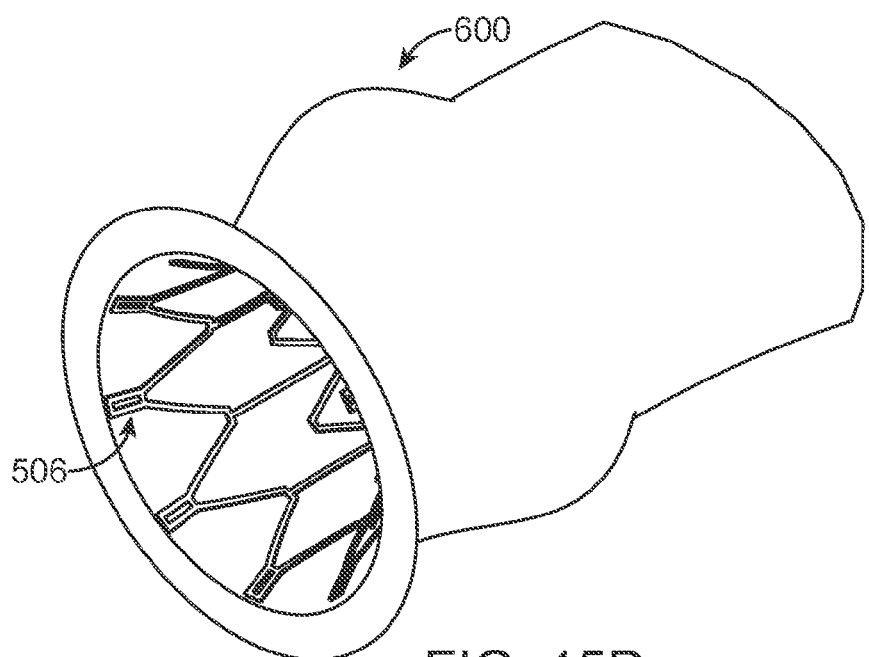

Once the prosthetic heart valve 504 has been satisfactorily located relative to the aortic valve 600, the tethers 514 are then withdrawn (FIG. 15C) followed by complete removal of delivery device 502 from the aortic valve 600. FIG. 15D illustrates final deployment of the stent frame assembly 506 to the aortic valve 600.

Although the present disclosure has been described with reference to preferred embodiments, workers skilled in the art will recognize that changes can be made in form and detail without departing from the spirit and scope of the present disclosure. For example, while various systems, devices and methods of the present disclosure have made reference to a self-expanding stent frame, features of the present disclosure are useful with other stented prosthetic heart valve constructions, such a balloon-expandable stent frame. In this regard, the tethered stent frame connections described above can be employed with a balloon-expandable stent frame, for example to facilitate a recapture operation whereby following expansion of the stent frame by a balloon, the tethers can be tensioned to effectuate at least partial collapsing of a corresponding region of the stent frame, that in turn promotes insertion (and more complete collapse) of an entirety of the stent frame within a recapture sheath or other component.

What is claimed is:

1. A system for performing a therapeutic procedure on a defective heart valve, the system comprising:
   a prosthetic heart valve including a stent frame maintaining a valve structure, the stent frame configured to provide a compressed condition and a natural, expanded condition; and
   a delivery device comprising:
   a handle,
   an inner shaft extending from the handle and terminating at a distal tip,
   a hub assembly carried by the inner shaft, the hub assembly including a valve retainer configured to selectively receive a component of the stent frame, the valve retainer including a capture feature, the capture feature including a post circumscribed by a groove,
   an outer sheath co-axially disposed over the inner shaft and including a capsule configured to contain the prosthetic heart valve,
   a first tether defining a length between opposing, first and second ends;
   wherein the system is configured to transition between:
   a delivery state in which the prosthetic heart valve is maintained over the inner shaft in the compressed condition by the capsule and the first tether is connected to the stent frame, wherein the stent frame defines opposing proximal and distal sides relative to the delivery device,
   a partial deployment state in which the capsule is withdrawn from the prosthetic heart valve and the first tether remains engaged with the stent frame and the stent frame expands toward the expanded condition with at least one of the proximal and distal sides connected to the delivery device via the first tether, the partial deployment state including expansion of at least one of the proximal and distal sides being controlled by a tension in the first tether,
   wherein the delivery and partial deployment states include the first tether forming a loop and opposing, first and second tether segments extending from opposite sides of the loop, the loop located within the groove and about the post, and the first and second tether segments extending from the post and routed through first and second crowns of the stent frame,
   a full deployment state in which the first tether is released from the stent frame.

2. The system of claim 1, wherein the first tether is connected to the proximal side of the stent frame in the delivery and partial deployment states.

3. The system of claim 1, wherein the first tether is connected to the distal side of the stent frame in the delivery and partial deployment states.

4. The system of claim 1, wherein the stent frame is a self-expanding stent frame configured to self-expand from the compressed condition to the normal, expanded condition.

5. The system of claim 1, wherein the stent frame is a balloon-expandable stent frame.

6. The system of claim 1, wherein the system is further configured to provide a recapture operation in the partial deployment state in which a tension in the first tether is increased and causes a corresponding region of the stent frame to partially re-collapse.

7. The system of claim 1, wherein the first tether is looped through a component of the stent frame in the delivery and partial deployment states.

8. The system of claim 1, wherein the system is configured such that the first tether self-releases from the stent frame in the partial deployment state such that the partial deployment state includes a tension in the tether allowing slow release of the stent frame.

9. The system of claim 8, wherein the first tether is wound about a component of the stent frame in the delivery state.

10. The system of claim 1, wherein the valve retainer is located proximate the distal tip.

11. The system of claim 1, wherein the valve retainer is located immediately proximate the proximal side of the prosthetic heart valve in the delivery state.

12. The system of claim 1, wherein the prosthetic heart valve defines a length in the compressed condition, and further wherein a longitudinal distance between the valve retainer and the distal tip approximates the length of the prosthetic heart valve.

13. The system of claim 1, wherein the first tether is one of a plurality of tethers provided with the delivery device, each of the plurality of tethers being connected to the proximal side of the prosthetic heart valve in the delivery and partial deployment states.

14. The system of claim 13, wherein the valve retainer defines a plurality of capture features, and further wherein each of the capture features is configured to selectively engage a corresponding one of the plurality of tethers.

15. The system of claim 12, wherein the system is configured such that partial deployment state includes a distal end of the capsule being located distal the capture feature of the valve retainer such that the capsule retains engagement between the first tether and the valve retainer.

16. The system of claim 1, wherein at least a portion of each of the first and second tether segments extending through a lumen of the inner shaft.

17. The system of claim 1, wherein the delivery and partial deployment states include the first and second tether segments routed from the post to the first crown, from the first crown to the second crown, and from the second crown to the lumen.

* * * * *